(12) United States Patent
Han et al.

(10) Patent No.: US 12,194,137 B2
(45) Date of Patent: Jan. 14, 2025

(54) BIOLOGICAL HAIR SHAPE CHANGE COMPOSITION AND KIT, AND METHOD FOR CHANGING HAIR SHAPE

(71) Applicant: Industrial Technology Research Institute, Hsinchu (TW)

(72) Inventors: Yin-Lung Han, Zhubei (TW);
Chieh-Lun Cheng, Taoyuan (TW);
Kai-Chun Fan, Zhushan Township (TW); Pei-Jyuan Gao, Tainan (TW);
Bo-Han Chen, Tainan (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 337 days.

(21) Appl. No.: 17/513,484

(22) Filed: Oct. 28, 2021

(65) Prior Publication Data
US 2023/0042170 A1    Feb. 9, 2023

(30) Foreign Application Priority Data

Jul. 16, 2021  (TW) .................................. 110126224

(51) Int. Cl.
| | |
|---|---|
| *A61K 8/99* | (2017.01) |
| *A61K 8/65* | (2006.01) |
| *A61K 8/66* | (2006.01) |
| *A61K 8/9778* | (2017.01) |
| *A61K 8/9789* | (2017.01) |
| *A61K 8/98* | (2006.01) |
| *A61Q 5/04* | (2006.01) |

(52) U.S. Cl.
CPC .................. *A61K 8/99* (2013.01); *A61K 8/65* (2013.01); *A61K 8/66* (2013.01); *A61K 8/9778* (2017.08); *A61K 8/9789* (2017.08); *A61K 8/985* (2013.01); *A61Q 5/04* (2013.01); *A61K 2800/591* (2013.01); *A61K 2800/78* (2013.01); *A61K 2800/85* (2013.01); *A61K 2800/882* (2013.01)

(58) Field of Classification Search
CPC .......... A61K 8/99; A61K 8/9778; A61K 8/65; A61K 8/66; A61K 8/985; A61K 2800/591; A61K 2800/78; A61K 2800/85; A61K 2800/882; A61Q 5/04
See application file for complete search history.

(56) References Cited

U.S. PATENT DOCUMENTS

| | | | |
|---|---|---|---|
| 5,529,926 A | 6/1996 | Maat et al. | |
| 8,232,066 B2 * | 7/2012 | Van Eyk | G01N 33/6848 |
| | | | 435/7.1 |
| 8,413,666 B2 * | 4/2013 | Presti | A45D 7/06 |
| | | | 424/70.2 |
| 9,084,734 B2 | 7/2015 | Collier et al. | |
| 2004/0180016 A1 | 9/2004 | Buck | |
| 2009/0081147 A1 | 3/2009 | Shibuya et al. | |
| 2010/0012142 A1 | 1/2010 | Presti | |
| 2016/0263000 A1 * | 9/2016 | Rautenberg-Groth | ...................... A61K 8/416 |

FOREIGN PATENT DOCUMENTS

| | | |
|---|---|---|
| CN | 102458352 A | 5/2012 |
| CN | 108078906 A | 5/2018 |
| JP | 2004-210700 A | 7/2004 |
| JP | 2005-15347 A | 1/2005 |
| JP | 2005015347 A * | 1/2005 |
| JP | 2008-540408 A | 11/2008 |
| JP | 2014-501761 A | 1/2014 |
| JP | 2015-503587 A | 2/2015 |
| KR | 10-2011-0135239 A | 12/2011 |

OTHER PUBLICATIONS

S.C.B. Gopinath, et al. Biotechnological Aspects and Perspective of Microbial Keratinase Production, BioMed Research International vol. 2015, Article ID 140726, 1-10. (Year: 2015).*
M. Huang, R. Chen, G. Ren. "Secretory expression and purification of Bacillus licheniformis keratinase in insect cells," PLoS ONE 12(8): e0183764 1-13, 2017. (Year: 2017).*
Online article "Bacillus licheniformis", downloaded Apr. 2, 2024 from https://web.archive.org/web/ 20210218083053/https://en.wikipedia.org/wiki/Bacillus_licheniformis, available Feb. 18, 2021. (Year: 2021).*
English Translation of JP2005015347A from EPO (Year: 2024).*
W. Kim, et al. "Purification and Characterization of a Fibrinolytic Enzyme Produced from Bacillus sp. strain CK 11-4 Screened from Chungkook-Jang," Applied and Environmental Microbiology, Jul. 1996, p. 2482-2488. (Year: 1996).*

(Continued)

*Primary Examiner* — Michael P Cohen

(74) *Attorney, Agent, or Firm* — Birch, Stewart, Kolasch & Birch, LLP

(57) ABSTRACT

A biological hair shape change composition including a macromolecular component, a small molecular component and an alkali agent component is provided. The macromolecular component includes a protease belonging to the class of alkaline proteases, and the small molecular component includes a peptide with reduction activity. Both the macromolecular component and the small molecular component are obtained from a fermentation product of *Bacillus licheniformis* and a keratin and/or keratin polymer-containing medium. Molecular weights of ingredients in the macromolecular component are greater than or equal to 3 kDa and are 3-1000 kDa, and molecular weights of ingredients in the small molecular component are less than 3 kDa and are 0.01-2.99 kDa.

36 Claims, 13 Drawing Sheets

Specification includes a Sequence Listing.

(56) References Cited

OTHER PUBLICATIONS

Sajna et al., "While Biotechnology in Cosmetics", Industrial Biorefineries & White Biotechnology, 1st Edition, Elsevier, May 8, 2015, pp. 607-652.
Taiwanese Office Action and Search Report for Taiwanese Application No. 110126224, dated Jul. 26, 2022.
Yang, "Application of Non-thermal Ultrasonic Technology in Food Extraction and Fermentation", Journal of Agriculture and Forestry, 2017, vol. 65, No. 3, pp. 125-136.
Japanese Office Action for Japanese Application No. 2022-106138, dated Oct. 27, 2023.

* cited by examiner

FIG. 6

BIOLOGICAL HAIR SHAPE CHANGE COMPOSITION AND KIT, AND METHOD FOR CHANGING HAIR SHAPE

CROSS REFERENCE TO RELATED APPLICATION

The present application is based on, and claims priority from, Taiwan Application Serial Number 110126224, filed Jul. 16, 2021, the disclosure of which is hereby incorporated by reference herein in its entirety.

INCORPORATION BY REFERENCE OF SEQUENCE LISTING

A sequence listing submitted as a text file via EFS-Web is incorporated herein by reference. The text file containing the sequence listing is named "9044E-A28041-US_Seq_Listing.txt"; its date of creation is Oct. 13, 2021; and its size is 4,065 bytes.

TECHNICAL FIELD

The technical field of the present disclosure relates to a biological hair shape change composition and a kit and a method for changing hair shape.

BACKGROUND

The commonly used perm method is achieved by changing the disulfide bonds in the keratin of the hair with a perm agent so that the hair can be reshaped. The steps of perming mainly include breaking the disulfide bonds in the keratin of the hair with a reducing agent, reshaping the hair with a styling tool, and permutating and forming the disulfide bonds with an oxidizing agent to allow the hair have the reshaped shape.

The currently used chemical perm agents are effective although they tend to cause scalp redness, skin irritation, skin allergies, and hair damage. Moreover, commercial chemical perm agents have the risk of inducing cancer. Although it is currently known that amino acid agents with fewer chemical components can be used for perming, their low damage to disulfide bonds makes hair styling less effective.

Therefore, there is an urgent need for a novel biological perm agent that can reduce the risk of skin redness, allergy, etc., and at the same time have a good shaping effect.

SUMMARY

The present disclosure provides a biological hair shape change composition comprising a macromolecular component, a small molecular component and an alkali agent component. The macromolecular component comprises a protease belonging to the class of alkaline proteases, and the small molecular component comprises a peptide with reduction activity. Both the macromolecular component and the small molecular component are obtained from a fermentation product of *Bacillus licheniformis* and a keratin and/or keratin polymer-containing medium. Molecular weights of ingredients in the macromolecular component are greater than or equal to 3 kDa and are 3-1000 kDa, and molecular weights of the ingredients in the small molecular component are less than 3 kDa and are 0.01-2.99 kDa.

The present disclosure also provides a biological hair shape change kit comprising a macromolecular component, a small molecular component, an alkali agent component and at least one packaging container for containing the macromolecular component, the small molecular component and the alkali agent component. The macromolecular component comprises a protease belonging to the class of alkaline proteases, and the small molecular component comprises a peptide with reduction activity. Both the macromolecular component and the small molecular component are obtained from a fermentation product of *Bacillus licheniformis* and a keratin and/or keratin polymer-containing medium. Moreover, molecular weights of ingredients in the macromolecular component are greater than or equal to 3 kDa and are 3-1000 kDa, and molecular weights of ingredients in the small molecular component are less than 3 kDa and are 0.01-2.99 kDa. The biological hair shape change kit is used in the form of a mixture of the macromolecular component, the small molecular component and the alkali agent component.

The present disclosure further provides a method for changing hair shape, comprising: (a) a hair penetration step, wherein the biological hair shape change composition mentioned above or a mixture produced by using the biological hair shape change kit mentioned above is applied to hair and allowed to penetrate into the hair; and (b) a hair shape changing step, wherein hair has been applied with and penetrated by the biological hair shape change composition mentioned above or the mixture mentioned above is subjected to a heating procedure to hydrolyze the backbone of a protein of the hair and break a disulfide bond in the protein of the hair to change the shape of the hair.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein:

FIG. 6 shows the results of skin sensitization analysis of the fermented primary liquid produced by *Bacillus licheniformis* GI_5E-1;

DETAILED DESCRIPTION

Figure 1:
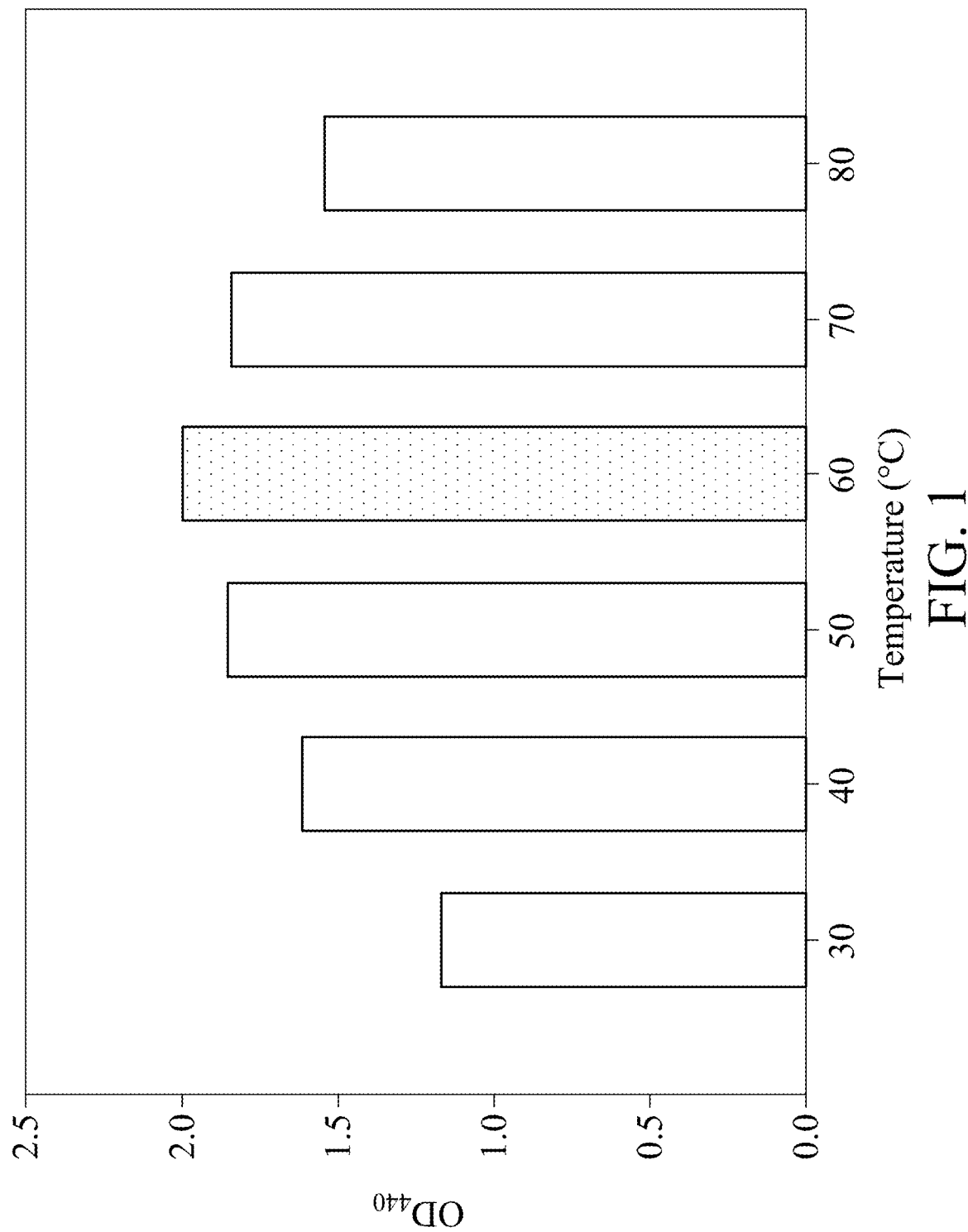
FIG. 1 shows the enzymatic activities of the fermented primary liquid produced by *Bacillus licheniformis* GI_5E-1 at different temperatures.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The present disclosure may provide a biological hair shape change composition, which is low-irritating or non-irritating, is hypoallergenic or non-allergenic, and has excellent hair shape change ability. The hair described herein may include any animal hair, and may be hair that still grows on the skin of an animal and/or has been separated from the animal, and has no particular limitation. In one embodiment, the hair described herein may be human hair, and in particular may be hair still growing on human skin.

The biological hair shape change composition of the present disclosure mentioned above may comprise, but is not limited to, a macromolecular component, a small molecular component and an alkali agent component.

Both the macromolecular component and small molecular component in the biological hair shape change composition of the present disclosure mentioned above may be obtained from a fermentation product of *Bacillus licheniformis* and a keratin and/or keratin polymer-containing medium.

The macromolecular composition in the biological hair shape change composition of the present disclosure mentioned above has no particular limitation, as long as it has the effect of hydrolyzing the backbone of a protein of hair (carbon-carbon chain), and the effects of the foregoing macromolecular composition in the biological hair shape change composition of the present disclosure is not only limited to hydrolyzing the backbone of a protein of hair (carbon-carbon chain).

Moreover, the macromolecular component in the biological hair shape change composition of the present disclosure mentioned above has excellent heat resistance and acid and alkali resistance. The macromolecular component in the biological hair shape change composition of the present disclosure mentioned above can maintain its effects in a wide temperature range, such as about 10-100° C. Furthermore, the macromolecular component in the biological hair shape change composition of the present disclosure mentioned above can maintain its effects in a wide pH range, such as about pH 3-12.

In one embodiment, the molecular weights of the ingredients in the macromolecular component mentioned above may be greater than or equal to about 3 kDa, such as greater than or equal to about 3.5 kDa, greater than or equal to about 4 kDa, greater than or equal to about 5 kDa, greater than or equal to about 10 kDa, greater than or equal to about 50 kDa, greater than or equal to about 100 kDa, greater than or equal to about 1000 kDa, about 3-1000 kDa, about 5-500 kDa, about 10-100 kDa, about 5 kDa, about 10 kDa, about 15 kDa, about 20 kDa, about 30 kDa, about 40 kDa, about 50 kDa, about 60 kDa, about 63 kDa, about 65 kDa, about 70 kDa, about 80 kDa, about 90 kDa, about 100 kDa, about 200 kDa, about 300 kDa, about 400 kDa, about 500 kDa, but it is not limited thereto. In one embodiment, the molecular weights of the ingredients in the macromolecular component mentioned above may be about 3-1000 kDa.

The macromolecular component mentioned above may comprise, but is not limited to, a protease belonging to the class of alkaline proteases. The protease belonging to the class of alkaline proteases mentioned above may have the effect of hydrolyzing the backbone (carbon-carbon chain) of a protein of hair, but it is not limited thereto. In one embodiment, the macromolecular component mentioned above may include alkaline proteases, keratinases, serine proteases, tyrosine proteases, etc. or any combination thereof, but it is not limited thereto. In one embodiment, the macromolecular component mentioned above may comprise alkaline protease. In another embodiment, the macromolecular component mentioned above may comprise keratinase. In yet another embodiment, the macromolecular component mentioned above may comprise a combination of alkaline protease and keratinase.

The molecular weight of the foregoing proteases belonging to the alkaline protease class may be greater than or equal to about 3 kDa, such as greater than or equal to about 3.5 kDa, greater than or equal to about 4 kDa, greater than or equal to about 5 kDa, greater than or equal to about 10 kDa, greater than or equal to about 50 kDa, greater than or equal to about 100 kDa, greater than or equal to about 1000 kDa, about 3-1000 kDa, about 5-500 kDa, about 10-100 kDa, about 5 kDa, about 10 kDa, about 15 kDa, about 20 kDa, about 30 kDa, about 40 kDa, about 50 kDa, about 60 kDa, about 63 kDa, about 65 kDa, about 70 kDa, about 80 kDa, about 90 kDa, about 100 kDa, about 200 kDa, about 300 kDa, about 400 kDa, about 500 kDa, etc., but it is not limited thereto. In one embodiment, the molecular weight of the foregoing protease belonging to the alkaline protease class may be about 3-1000 kDa. In another embodiment, the molecular weight of the foregoing protease belonging to the class of alkaline proteases may be about 63 kDa. In one specific embodiment, the foregoing protease belonging to the class of alkaline proteases is an alkaline protease, keratinase or a combination thereof with a molecular weight of about 63 kDa.

Furthermore, the content of the foregoing alkaline proteases in the biological hair shape change composition of present disclosure may be about 150-3000 U/mL, such as about 200 U/mL, about 215 U/mL, about 230 U/mL, about 250 U/mL, about 300 U/mL, about 315 U/mL, about 320 U/mL, about 330 U/mL, about 333 U/mL, about 350 U/mL, about 400 U/mL, about 500 U/mL, about 1000 U/mL, about 1500 U/mL, about 2000 U/mL, about 2500 U/mL, about 3000 U/mL, but it is not limited thereto.

The small molecular component in the biological hair shape change composition of the present disclosure mentioned above also has no particular limitation, as long as it is capable of breaking a disulfide bond of a protein of hair, and the effects of the foregoing small molecular component in the biological hair shape change composition of the present disclosure is not only limited to breaking a disulfide bond of a protein of hair.

The molecular weights of the ingredients in the small molecular component mentioned above may be less than about 3 kDa, such as less than about 2.99 kDa, less than about 2.5 kDa, less than about 2 kDa, less than about 1 kDa, less than about 0.5 kDa, about 0.01-2.99 kDa, about 0.1-2.8 kDa, about 0.5-2.7 kDa, about 1-2.6 kDa, about 1.2-2.5 kDa, about 0.5 kDa, about 0.55 kDa, about 1.1 kDa, about 1.2 kDa, about 1.3 kDa, about 1.4 kDa, about 1.5 kDa, about 1.6 kDa, about 1.7 kDa, about 1.8 kDa, about 1.9 kDa, about 2.0 kDa, about 2.1 kDa, about 2.2 kDa, about 2.3 kDa, about 2.4 kDa, about 2.5 kDa, about 2.6 kDa, about 2.7 kDa, about 2.8 kDa, about 2.9 kDa, about 2.95 kDa, about 2.99 kDa, but it is not limited thereto. In one embodiment, the molecular weights of the ingredients in the small molecular component mentioned above may be about 0.01-2.99 kDa.

The small molecular component may comprise, but is not limited to, a peptide with reduction activity. In addition to reduction activity, the peptide with reduction activity mentioned above may further break a disulfide bond of a protein of hair, however, its effects are not limited thereto.

The length of the peptide with reduction activity mentioned above may be about 5-30 amino acids, such as about 6-28 amino acids, about 11-25 amino acids, about 10 amino acids, about 11 amino acids, about 12 amino acids, about 13 amino acids, about 14 amino acids, about 15 amino acids, about 20 amino acids, about 23 amino acids, about 25 amino acids, about 30 amino acids, but it is not limited thereto.

Moreover, the peptide with reduction activity mentioned above may comprise, but is not limited to, at least one the following peptides:

(a) a peptide comprising the amino acid sequence of SEQ ID NO. 1;
(b) a peptide comprising the amino acid sequence of SEQ ID NO. 2;
(c) a peptide comprising the amino acid sequence of SEQ ID NO. 3;
(d) a peptide comprising the amino acid sequence of SEQ ID NO. 4;
(e) a peptide comprising the amino acid sequence of SEQ ID NO. 5;
(f) a peptide comprising the amino acid sequence of SEQ ID NO. 6;
(g) a peptide comprising the amino acid sequence of SEQ ID NO. 7;
(h) a peptide comprising the amino acid sequence of SEQ ID NO. 8;
(i) a peptide comprising the amino acid sequence of SEQ ID NO. 9; and
(j) a peptide comprising the amino acid sequence of SEQ ID NO. 10.

In one embodiment, the foregoing small molecular component may comprise the foregoing peptide comprising the amino acid sequence of SEQ ID NO. 2. In another embodiment, the foregoing small molecular component may comprise the foregoing peptide comprising the amino acid sequence of SEQ ID NO. 3. In yet another embodiment, the foregoing small molecular component may comprise the foregoing peptide comprising the amino acid sequence of SEQ ID NO. 6. In yet another embodiment, the foregoing small molecular component may comprise the foregoing peptide comprising the amino acid sequence of SEQ ID NO. 10. In one specific embodiment, the foregoing small molecular component may comprise the foregoing peptide comprising the amino acid sequence of SEQ ID NO. 2, the foregoing peptide comprising the amino acid sequence of SEQ ID NO. 3, the foregoing peptide comprising the amino acid sequence of SEQ ID NO. 6 and the foregoing peptide comprising the amino acid sequence of SEQ ID NO. 10. In another specific embodiment, the foregoing small molecular component may comprise the foregoing peptide comprising an amino acid sequence of SEQ ID NO. 1, the foregoing peptide comprising an amino acid sequence of SEQ ID NO. 2, the foregoing peptide comprising an amino acid sequence of SEQ ID NO. 3, the foregoing peptide comprising an amino acid sequence of SEQ ID NO. 4, the foregoing peptide comprising an amino acid sequence of SEQ ID NO. 5, the foregoing peptide comprising an amino acid sequence of SEQ ID NO. 6, the foregoing peptide comprising an amino acid sequence of SEQ ID NO. 7, the foregoing peptide comprising an amino acid sequence of SEQ ID NO. 8, the foregoing peptide comprising an amino acid sequence of SEQ ID NO. 9 and the foregoing peptide comprising an amino acid sequence of SEQ ID NO. 10.

In addition, the foregoing fermentation product of *Bacillus licheniformis* and a keratin and/or keratin polymer-containing medium, from which the macromolecular component and the small molecular component of the biological hair shape change composition of the present disclosure can be obtained, is further described as below.

*Bacillus licheniformis* involving the foregoing fermentation product of *Bacillus licheniformis* and a keratin and/or keratin polymer-containing medium has no particular limitation, as long as the macromolecular component and the small molecular component of the biological hair shape change composition of the present disclosure can be obtained therefrom. The foregoing *Bacillus licheniformis* may comprise *Bacillus licheniformis* BCRC 14353, *Bacillus licheniformis* GI_5E-1 which was deposited in China Center for Type Culture Collection (CCTCC) on Aug. 17, 2021, and the deposit number of which is CCTCC M 20211045, etc., or any combination thereof, but it is not limited thereto. In one embodiment, the *Bacillus licheniformis* involving the foregoing fermentation product of *Bacillus licheniformis* and a keratin and/or keratin polymer-containing medium may be *Bacillus licheniformis* BCRC 14353. In another embodiment, the *Bacillus licheniformis* involving the foregoing fermentation product of *Bacillus licheniformis* and a keratin and/or keratin polymer-containing medium may be *Bacillus licheniformis* GI_5E-1 which was deposited in China Center for Type Culture Collection (CCTCC) on Aug. 17, 2021, and the deposit number of which is CCTCC M 20211045.

Furthermore, the keratin and/or keratin polymer-containing medium mentioned above may comprise, but is not limited to, a keratin and/or keratin polymer-containing substrate. The content of the foregoing keratin and/or keratin polymer-containing substrate in the foregoing keratin and/or keratin polymer-containing medium may be about 0.01-20 g/L, such as about 0.02-15 g/L, about 0.05-10 g/L, about 1-5 g/L, about 0.01 g/L, about 0.05 g/L, about 0.1 g/L, about 0.5 g/L, about 1 g/L, about 2 g/L, about 4 g/L, about 5 g/L, about 6 g/L, about 8 g/L, about 10 g/L, but it is not limited thereto. In one embodiment, the content of the foregoing keratin and/or keratin polymer-containing substrate in the foregoing keratin and/or keratin polymer-containing medium may be about 10 g/L.

In addition, the foregoing keratin and/or keratin polymer-containing substrate may comprise animal feathers, hair, hooves, claws, horns, etc., or any combination thereof, but it is not limited thereto. The foregoing animal feathers, hairs, hooves, claws, horns, etc. may also be discarded animal feathers, hairs, hooves, claws, horns, etc. In the case where the foregoing keratin and/or keratin polymer-containing substrate may comprise discarded animal feathers, hairs, hooves, claws, horns, etc., or any combination thereof, since the macromolecular component and the small molecular component in the biological hair shape change composition of the present disclosure mentioned above are obtained by waste, the method of obtaining the macromolecular component and the small molecular component in the biological hair shape change composition of the present disclosure can be regarded as a method for recycling and reusing waste and has the effect of environmental protection. In one embodiment, the foregoing keratin and/or keratin polymer-containing substrate may comprise feathers. In one specific embodiment, the foregoing keratin and/or keratin polymer-containing substrate may comprise discarded feathers. In the specific embodiment in which the foregoing keratin and/or keratin polymer-containing substrate may comprise discarded feathers, the content of discarded feathers in the keratin and/or keratin polymer-containing medium may be about 0.01-20 g/L, such as about 0.02-15 g/L, about 0.05-10 g/L, about 1-5 g/L, about 0.01 g/L, about 0.05 g/L, about 0.1 g/L, about 0.5 g/L, about 1 g/L, about 2 g/L, about 4 g/L, about 5 g/L, about 6 g/L, about 8 g/L, about 10 g/L, but it is not limited thereto.

Furthermore, the foregoing fermentation product of *Bacillus licheniformis* and a keratin and/or keratin polymer-containing medium may be obtained by culturing the foregoing *Bacillus licheniformis* with the foregoing keratin and/or keratin polymer-containing medium. The temperature for culturing the foregoing *Bacillus licheniformis* may be about 25-70° C., such as about 30-45° C., about 45-55° C., about 55-65° C., about 30° C., about 35° C., about 37° C., about 40° C., about 45° C., about 50° C., about 55° C., about 60° C., about 65° C., but it is not limited thereto. The time for culturing the foregoing *Bacillus licheniformis* may be about 24-96 hours, such as about 48-72 hours, about 24 hours, about 48 hours, about 72 hours, about 96 hours, but it is not limited thereto.

The macromolecular component and small molecular component in the biological hair shape change composition of the present disclosure mentioned above may be obtained by after obtaining the foregoing fermentation product of *Bacillus licheniformis* and a keratin and/or keratin polymer-containing medium, filtering the fermentation product through a film capable of separating the ingredients with molecular weights greater than or equal to 3 kDa from the ingredients with molecular weights less than 3 kDa, but it is not limited thereto.

In addition, the foregoing small molecular component may be further mixed with a new keratin and/or keratin polymer-containing substrate to form a mixture, and cultured to increase the reduction activity and/or effects of breaking a disulfide bond of a protein of hair of the small molecular component. The related description of the new keratin and/or keratin polymer-containing substrate described herein may be the same as that of the foregoing keratin and/or keratin polymer-containing substrate, and thus is not repeated herein. The content of the new keratin and/or keratin polymer-containing substrate in the mixture mentioned above is about 0.05-2% (w/v), such as about 0.1-1% (w/v), about 0.2-0.8% (w/v), about 0.1% (w/v), about 0.2% (w/v), about 0.5% (w/v), about 0.8% (w/v), about 1% (w/v), but it is not limited thereto.

The alkali agent component in the biological hair shape change composition of the present disclosure may comprise a plant-derived alkali agent, a chemical synthesis-derived alkali agent, or a combination thereof, but it is not limited thereto.

The concentration of the alkali agent component mentioned above in the biological hair shape change composition of the present disclosure mentioned above may be about 1-80% (v/v), such as about 5-60% (v/v), about 10-50% (v/v), about 5% (v/v), about 10% (v/v), about 15% (v/v), about 25% (v/v), about 30% (v/v), about 50% (v/v), but it is not limited thereto.

The foregoing plant-derived alkali agent has no particular limitation, as long as it belongs to an alkali agent derived from a plant source. The foregoing plant-derived alkali agent may have the effect of increasing the disulfide bond breaking efficiency of the small molecular component, but it is not limited thereto. The foregoing plant-derived alkali agent may comprise, but is not limited to, at least one of the following plant-derived alkali extracts: a coffee grounds extract, a tea stems extract, a mulberry leaf extract, etc. or any combination thereof. The foregoing plant-derived extract may be a plant-derived water extract, but it is not limited thereto. In one embodiment, the foregoing plant-derived alkali agent may comprise at least one of the following plant-derived extracts: a water extract of coffee grounds, a water extract of a tea stems, a water extract of a mulberry leaf, etc., but it is not limited thereto. The water extract of coffee grounds may comprise, but is not limited to, nicotine, etc. The water extract of tea stems may comprise, but is not limited to, theophylline, and the water extract of mulberry leaf may comprise, but is not limited to, plant alkaloids. In one specific embodiment, the alkali agent component in the biological hair shape change composition of the present disclosure may be a water extract of coffee grounds. Coffee grounds, tea stems, etc. are usually regarded as waste, and the alkali agent of the biological hair shape change composition of the present disclosure can be obtained from waste, so that the waste can be recycled and reused. Therefore, the biological hair shape change composition of the present disclosure may have the effect of environmental protection.

In addition, the foregoing chemical synthesis-derived alkali agent may comprise, but is not limited to, at least one of the following ingredients: nicotine, theophylline, plant alkaloid, ammonia, etc.

Furthermore, in the biological hair shape change composition of the present disclosure, the volume ratio of the foregoing macromolecular component to the foregoing small molecular component may be about 5-10:1.5-3, but it is not limited thereto. In one embodiment, in the biological hair shape change composition of the present disclosure, the volume ratio of the foregoing macromolecular component to the foregoing small molecular component may be about 5:1.5. In another embodiment, in the biological hair shape change composition of the present disclosure, the volume ratio of the foregoing macromolecular component to the foregoing small molecular component may be about 10:3.

In one embodiment, the biological hair shape change composition of the present disclosure may further comprise additional water. The additional water mentioned above may comprise tap water, RO water, pure water, etc., but it is not limited thereto.

The present disclosure may also provide a biological hair shape change kit, which is used to change hair shape, is low irritation or non-irritation, and is hypoallergenic or non-allergenic, and has excellent hair shape change ability. The hair described herein may include any animal hair, and may be hair that still grows on the skin of an animal and/or has been separated from the animal, and has no particular limitation. In one embodiment, the hair described herein may be human hair, and in particular may be hair still growing on human skin.

The biological hair shape change kit of the present disclosure mentioned above may comprise a macromolecular component, a small molecular component, an alkali component and at least one packaging container, but it is not limited thereto. In addition, the biological hair shape change kit of the present disclosure may be used in the form of a mixture of the foregoing macromolecular component, the foregoing small molecular component and the foregoing alkali agent component.

The macromolecular component, the small molecular component and the alkali agent component in the biological hair shape change kit of the present disclosure mentioned above can be the same as the macromolecular component, the small molecular component and the alkali agent component in the biological hair shape change composition of the present disclosure mentioned above, and thus the related description thereof is not repeated herein.

The at least one packaging container in the biological hair shape change kit of the present disclosure is used to contain the foregoing macromolecular composition, the foregoing small molecular composition and the foregoing alkaline composition. The material of the least one packaging container mentioned above has no particular limitation, as long as it is not affected by the foregoing macromolecular composition, the foregoing small molecular composition, the foregoing alkali agent component or any combination thereof, and/or it does not adversely affect the effects of the foregoing macromolecular composition, the foregoing small molecular composition, the foregoing alkali agent component or any combination thereof. The material of the foregoing at least one packaging containers may comprise, but is not limited to, glass, plastic, ceramic, etc., a composite material formed of any materials mentioned above, or any combination of the materials mentioned above.

In one embodiment, in the biological hair shape change kit of the present disclosure mentioned above, the macromolecular component mentioned above may be contained in a first reagent, the small molecular component mentioned above may be contained in a second reagent, and the alkali agent component mentioned above may be contained in a third reagent, and the at least one packaging container mentioned above may comprise a first container, a second container and a third container, wherein the foregoing first reagent may be packaged in the foregoing first container, the foregoing second reagent may be packaged in the foregoing second container and the foregoing third reagent may be packaged in the foregoing third container. Furthermore, in this embodiment, the biological hair shape change kit of the present disclosure may be used in the form of a mixture of the foregoing first reagent, the foregoing second reagent and the foregoing third reagent. In one usage scenario for this embodiment, the biological hair shape change kit of the present disclosure mentioned above may be used by mixing the foregoing first reagent, the foregoing second reagent, the foregoing third reagent and additional water (e.g., tap water, RO water, purified water, but it is not limited thereto) in a specific volume ratio. The foregoing specific volume ratio may be about 5-10:1.5-3:3-6:1-10.5, such as about 5:1.5:3: 10.5, about 5:1.5:6:7.5, about 10:3:6:1, but it is not limited thereto. In another usage scenario for this embodiment, the biological hair shape change kit of the present disclosure mentioned above may be used by respectively pouring the first reagent, the second reagent, and the third reagent all out of the first container, the second container, and the third container, and mixing them with additional water. In yet another usage scenario for this embodiment, the biological hair shape change kit of the present disclosure mentioned above may be used by respectively pouring the foregoing first reagent and the foregoing second reagent all out of the foregoing first container and the foregoing second container to the foregoing third container and adding water to the foregoing third container to allow the foregoing first reagent, the foregoing second reagent, the foregoing third reagent and water be mixed in the foregoing third container, or by respectively pouring the foregoing first reagent and the foregoing third reagent all out of the foregoing first container and the foregoing third container to the foregoing second container and adding water to the foregoing second container to allow the foregoing first reagent, the foregoing second reagent, the foregoing third reagent and water be mixed in the foregoing second container, or by respectively pouring the foregoing second reagent and the foregoing third reagent all out of the foregoing second container and the foregoing third container to the foregoing first container and adding water to the foregoing first container to allow the foregoing first reagent, the foregoing second reagent, the foregoing third reagent and water be mixed in the foregoing first container. In addition, in this embodiment, the biological hair shape change kit of the present disclosure may further comprise a mixing container for containing and mixing the foregoing first reagent, the foregoing second reagent and the foregoing third reagent poured out of the foregoing first container, the foregoing second container, and the foregoing third container, respectively, and water. The material of the mixing container has no particular limitation, as long as it is not affected by the mixture of the foregoing first reagent, the foregoing second reagent, the foregoing third reagent and water, and/or it does not adversely affect the effect of the mixture of the foregoing first reagent, the foregoing second reagent, the foregoing third reagent and water during using of the kit. The material of the mixing container may comprise glass, plastic, ceramic, paper, etc., a composite material formed of any materials mentioned above, or any combination of the materials mentioned above.

In another embodiment, in the biological hair shape change kit of the present disclosure mentioned above, the macromolecular component mentioned above and the small molecular component mentioned above may be contained in a first reagent, and the alkali agent component mentioned above may be contained in a second reagent, and the at least one packaging container mentioned above may comprise a first container and a second container, wherein the foregoing first reagent may be packaged in the foregoing first container and the foregoing second reagent may be packaged in the foregoing second container. Furthermore, in this embodiment, the biological hair shape change kit of the present disclosure may be used in the form of a mixture of the foregoing first reagent and the foregoing second reagent. In one usage scenario for this embodiment, the biological hair shape change kit of the present disclosure mentioned above may be used by mixing the foregoing first reagent, the foregoing second reagent and additional water (e.g., tap water, RO water, purified water, but it is not limited thereto) in a specific volume ratio. The foregoing specific volume ratio may be about 6.5-13:3-6:1-10.5, such as about 6.5:3: 10.5, about 6.5:6:7.5, about 13:6:1, but it is not limited thereto. In another usage scenario for this embodiment, the biological hair shape change kit of the present disclosure mentioned above may be used by respectively pouring the first reagent and the second reagent all out of the first container and the second container, and mixing them with additional water. In yet another usage scenario for this embodiment, the biological hair shape change kit of the present disclosure mentioned above may be used by pouring the foregoing first reagent all out of the foregoing first container to the foregoing second container and adding water to the foregoing second container to allow the foregoing first reagent, the foregoing second reagent and water be mixed in the foregoing second container, or by pouring the foregoing second reagent all out of the foregoing second container to the foregoing first container and adding water to the foregoing first container to allow the foregoing first reagent, the foregoing second reagent and water be mixed in the foregoing first container. In addition, in this embodiment, the biological hair shape change kit of the present disclosure may further comprise a mixing container for containing and mixing the foregoing first reagent, and the foregoing second reagent poured out of the foregoing first container and the foregoing second container, respectively, and water. The material of the mixing container has no particular limitation, as long as it is not affected by the mixture of the foregoing first reagent, the foregoing second reagent and water, and/or it does not adversely affect the effect of the mixture of the foregoing first reagent, the foregoing second reagent and water during using of the kit. The material of the mixing container may comprise glass, plastic, ceramic, paper, etc., a composite material formed of any materials mentioned above, or any combination of the materials mentioned above.

In yet another embodiment, in the biological hair shape change kit of the present disclosure mentioned above, the macromolecular component mentioned above may be contained in a first reagent, and the small molecular component mentioned above and the alkali agent component mentioned above may be contained in a second reagent, and the at least one packaging container mentioned above may comprise a first container and a second container, wherein the foregoing first reagent may be packaged in the foregoing first container and the foregoing second reagent may be packaged in the foregoing second container. Furthermore, in this embodiment, the biological hair shape change kit of the present disclosure may be used in the form of a mixture of the foregoing first reagent and the foregoing second reagent. In one usage scenario for this embodiment, the biological hair shape change kit of the present disclosure mentioned above may be used by mixing the foregoing first reagent, the foregoing second reagent and additional water (e.g., tap water, RO water, purified water, but it is not limited thereto) in a specific volume ratio. The foregoing specific volume ratio may be about 1-10:0.9-9:1-2.1, such as about 1:0.9:2.1, about 1:1.5:1.5, about 10:9:1, but it is not limited thereto. In another usage scenario for this embodiment, the biological hair shape change kit of the present disclosure mentioned above may be used by respectively pouring the first reagent and the second reagent all out of the first container and the second container, and mixing them with additional water. In yet another usage scenario for this embodiment, the biological hair shape change kit of the present disclosure mentioned above may be used by pouring the foregoing first reagent all out of the foregoing first container to the foregoing second container and adding water to the foregoing second container to allow the foregoing first reagent, the foregoing second reagent and water be mixed in the foregoing second container, or by pouring the foregoing second reagent all out of the foregoing second container to the foregoing first container and adding water to the foregoing first container to allow the foregoing first reagent, the foregoing second reagent and water be mixed in the foregoing first container. In addition, in this embodiment, the biological hair shape change kit of the present disclosure may further comprise a mixing container for containing and mixing the foregoing first reagent, and the foregoing second reagent poured out of the foregoing first container and the foregoing second container, respectively, and water. The material of the mixing container has no particular limitation, as long as it is not affected by the mixture of the foregoing first reagent, the foregoing second reagent and water, and/or it does not adversely affect the effect of the mixture of the foregoing first reagent, the foregoing second reagent and water during using of the kit. The material of the mixing container may comprise glass, plastic, ceramic, paper, etc., a composite material formed of any materials mentioned above, or any combination of the materials mentioned above.

In yet another embodiment, in the biological hair shape change kit of the present disclosure mentioned above, the macromolecular component mentioned above and the alkali agent component mentioned above may be contained in a first reagent, and the small molecular component mentioned above may be contained in a second reagent, and the at least one packaging container mentioned above may comprise a first container and a second container, wherein the foregoing first reagent may be packaged in the foregoing first container and the foregoing second reagent may be packaged in the foregoing second container. Furthermore, in this embodiment, the biological hair shape change kit of the present disclosure may be used in the form of a mixture of the foregoing first reagent and the foregoing second reagent. In one usage scenario for this embodiment, the biological hair shape change kit of the present disclosure mentioned above may be used by mixing the foregoing first reagent, the foregoing second reagent and additional water (e.g., tap water, RO water, purified water, but it is not limited thereto) in a specific volume ratio. The foregoing specific volume ratio may be about 8-16:1.5-3:1-10.5, such as about 8:1.5:10.5, about 11:1.5:7.5, about 16:3:1, but it is not limited thereto. In another usage scenario for this embodiment, the biological hair shape change kit of the present disclosure mentioned above may be used by respectively pouring the first reagent and the second reagent all out of the first container and the second container, and mixing them with additional water. In yet another usage scenario for this embodiment, the biological hair shape change kit of the present disclosure mentioned above may be used by pouring the foregoing first reagent all out of the foregoing first container to the foregoing second container and adding water to the foregoing second container to allow the foregoing first reagent, the foregoing second reagent and water be mixed in the foregoing second container, or by pouring the foregoing second reagent all out of the foregoing second container to the foregoing first container and adding water to the foregoing first container to allow the foregoing first reagent, the foregoing second reagent and water be mixed in the foregoing first container. In addition, in this embodiment, the biological hair shape change kit of the present disclosure may further comprise a mixing container for containing and mixing the foregoing first reagent, and the foregoing second reagent poured out of the foregoing first container and the foregoing second container, respectively, and water. The material of the mixing container has no particular limitation, as long as it is not affected by the mixture of the foregoing first reagent, the foregoing second reagent and water, and/or it does not adversely affect the effect of the mixture of the foregoing first reagent, the foregoing second reagent and water during using of the kit. The material of the mixing container may comprise glass, plastic, ceramic, paper, etc., a composite material formed of any materials mentioned above, or any combination of the materials mentioned above.

Furthermore, in one embodiment, in the biological hair shape change kit of the present disclosure mentioned above, the macromolecular component mentioned above, the small molecular component mentioned above and the alkali agent component mentioned above may be contained in a first reagent, and the at least one packaging container mentioned above may comprise a first container, wherein the first reagent mentioned above may be packaged in the first container mentioned above. In this embodiment, the biological hair shape change kit of the present disclosure mentioned above can be used by directly using the foregoing first reagent, or by mixing the foregoing first reagent with water, and the volume ratio of the foregoing first reagent to water is about 1:0.05-1.1, but it is not limited thereto.

In addition, in one embodiment, the biological hair shape change kit of the present disclosure mentioned above may further comprise an oxidizing agent for fixing the shape of the hair that has been changed shape. Examples of oxidizing agents applicable to the biological hair shape change kit of the present disclosure mentioned above may comprise, but is not limited to, sodium bromate and hydrogen peroxide. Moreover, in this embodiment, the oxidizing agent may be packaged in a packaging container different from that for packaging the macromolecular component mentioned above, the small molecular component mentioned above, the alkali agent component mentioned above, or any combination thereof.

In addition, in one embodiment, the biological hair shape change kit of the present disclosure, in addition to the macromolecular component mentioned above, the small molecular component mentioned above and the alkali agent component mentioned above may further comprise additional water. The additional water mentioned above may comprise tap water, RO water, pure water, etc., but it is not limited thereto.

Furthermore, according to the foregoing, the present disclosure can also provide a method for changing hair shape, which can be performed through any biological hair shape change composition of the present disclosure mentioned above or through a mixture resulting from using any biological hair shape change kit of the present disclosure mentioned above. The hair used in the method for changing hair shape of the present disclosure may include any animal hair, and may be hair that still grows on the skin of an animal and/or has been separated from the animal, and has no particular limitation. In one embodiment, the hair described herein may be human hair, and in particular may be hair still growing on human skin.

Through any biological hair shape change composition of the present disclosure mentioned above or through a mixture resulting from using any biological hair shape change kit of the present disclosure mentioned above, compared to the a conventional method for changing hair shape, the method of the present disclosure can achieve an effect of effectively changing shape at a lower temperature, and while the hair still grows on an animal body, it does not or is less likely to cause irritation and/or allergic reactions to the skin or eyes, etc. of the animal body.

The method for changing hair shape of the present disclosure mentioned above may comprise a hair penetration step and a hair shape changing step, but it is not limited thereto.

In the foregoing hair penetration step, any biological hair shape change composition of the present disclosure mentioned above or a mixture resulting from using any biological hair shape change kit of the present disclosure mentioned above can be applied to the hair and allowed to penetrate into the hair.

The time for performing the foregoing hair penetration step can be based on the properties of the hair to be treated (such as thickness, hardness and curl), the current condition of the hair to be treated (such as the health, dryness of the hair), the amount of hair to be treated, and the environmental conditions (such as temperature and humidity) for treating the hair, and has no particular limitation, as long as the biological hair shape change composition of the present disclosure mentioned above or the mixture resulting from using the biological hair shape change kit of the present disclosure mentioned above can penetrate into the hair. In one embodiment, the time for performing the foregoing hair penetration step may be about 1-60 minutes, such as about 5 minutes, about 10 minutes, about 15 minutes, about 20 minutes, about 30 minutes and about 60 minutes, but it is not limited thereto.

Furthermore, the hair penetration step mentioned above may be performed at room temperature, but it is not limited thereto.

In addition, in the foregoing hair shape changing step, a heating procedure can be performed on hair that has been applied with and penetrated by the biological hair shape change composition of the present disclosure mentioned above or the mixture resulting from using the biological hair shape change kit of the present disclosure mentioned above to hydrolyze the backbone of a protein of the hair and break a disulfide bonds in a protein of the hair to change the shape of the hair.

The temperature of the heating procedure may be about 40-100° C., such as about 40° C., about 50° C., about 60° C., about 70° C., about 90° C., and about 100° C., but it is not limited thereto. In one embodiment, the temperature of the heating procedure may be about 60° C.

The time for performing the foregoing hair shape changing step can be based on the properties of the hair to be treated (such as thickness, hardness and curl), the current condition of the hair to be treated (such as the health, dryness of the hair), the amount of hair to be treated, and the environmental conditions (such as temperature and humidity) for treating the hair, and has no particular limitation, as long as the shape of the hair can be changed. In one embodiment, the time for performing the foregoing hair shape changing step may be about 1-60 minutes, such as about 5 minutes, about 10 minutes, about 15 minutes, about 20 minutes, about 30 minutes and about 60 minutes, but it is not limited thereto.

In one embodiment, the method for changing hair shape of the present disclosure, in addition to the hair penetration step and the hair shape changing step mentioned above, may further comprise a step of wetting the hair before the hair penetration step mentioned above.

In one embodiment, the method for changing hair shape of the present disclosure, in addition to the hair penetration step and the hair shape changing step mentioned above, may further comprise a step of cleaning the hair after the hair shape changing step mentioned above.

Moreover, in one embodiment, the method for changing hair shape of the present disclosure may be a perm treatment method. In this embodiment, the method for changing hair shape of the present disclosure, in addition to the hair penetration step and the hair shape changing step mentioned above, may further comprise the step of winding the hair in a hair curl before the hair penetration step mentioned above.

In another embodiment, the method for changing hair shape of the present disclosure may be a curly hair straightening treatment method. In this embodiment, the method for changing hair shape of the present disclosure, in addition to the hair penetration step and the hair shape changing step mentioned above may simultaneously perform the heating procedure mentioned and a procedure of straightening curly hair during the hair shape changing step mentioned above.

Moreover, in one embodiment, the method for changing hair shape of the present disclosure, in addition to the hair penetration step and the hair shape changing step mentioned above, may further comprise a step of fixing the shape of the hair after the hair shape changing step. The step of fixing the shape of the hair mentioned above may comprise, but it is not limited to, applying an oxidizing agent to the hair of which the shape is changed, but it is not limited thereto.

EXAMPLES

A. Experimental Methods
1. Culture of Bacterial Strain

Culture of bacterial strain was performed by LB medium (Difco™ LB Broth, Miller; BD), and 2% agar (Bacto™ agar; BD) was added to the LB medium to prepare an LB culture plate.

The cryogenic storage vial of the strain (*Bacillus licheniformis* BCRC 14353 purchased from Bioresource Collection and Research Center (BCRC) of Food industry research and development institute (FIRDI), Republic of China (Taiwan), or *Bacillus licheniformis* GI_5E-1 which was deposited in China Center for Type Culture Collection (CCTCC) on Aug. 17, 2021, and the deposit number of which is CCTCC M 20211045) was subjected to the quadrant streak method on a LB agar plate, and in a 50° C. constant temperature shaking incubator (LM-420D; YIH DER) for static culture 24 hours.

After that, a single colony was picked from the culture plate and inoculated into a 50 mL centrifuge tube containing 10 mL LB culture solution, and the centrifuge tube was placed at an inclination of 45 degrees in a 50° C. constant temperature incubator and incubated at 150 rpm for 24 hours to obtain a cultured bacterial suspension.

The bacterial suspension mentioned above was diluted to an optical density (optical density, OD) at 600 nm ($OD_{600}$) of 0.08-0.1 measured by a spectrophotometer (SP-880; Metertech), and then 1 mL diluted bacterial suspension was taken to inoculate into a 250 mL Erlenmeyer flask containing 150 mL feather medium (Lin, X., Lee, C G, Casale, E S, & Shih, J C (1992). Purification and characterization of a keratinase from a feather-degrading *Bacillus licheniformis* strain. Applied and environmental microbiology, 58(10), 3271-3275), placed in a 50° C. constant temperature shaking incubator, and incubated at 150 rpm for 72 hours to perform an enzyme production induction culture to obtain a cultured bacterial medium. The formula of feather medium is shown in Table 1.

TABLE 1

Formula of feather culture medium

| Ingredient | Concentration (g/L) |
| --- | --- |
| $NH_4Cl$ | 0.5 |
| NaCl | 0.5 |
| $K_2HPO_4$ | 0.3 |
| $KH_2PO_4$ | 0.4 |
| $MgCl_2 \cdot 6H_2O$ | 0.1 |
| Yeast Extract | 0.1 |
| Feather | 10 |

The cultured bacterial medium mentioned above was centrifuged at 12,000×g at 4° C. for 10 minutes by a refrigerated centrifuge (Centrifuge 5804 R; Eppendorf) to remove large particles of feather meal and retain the supernatant. Then, the supernatant was filtered by suction filtration with 0.8 μm and 0.45 μm membrane filters (Membrane filter; Advantec) in order, and then further filtered with 0.22 μm filter cups (Vacuum Filtra; Biofil) to obtain a filtrate. This filtrate is defined as fermented primary liquid.

The fermented primary liquid was separated and purified using a protein concentration system (KrosFlo KR2i TFF System; Spectrum) (column model 504-E001-05-N) (molecules with molecular weight less than 3 kDa could be filtered out from the hollow fiber membrane of the column); flow rate: 500 mL/minute; back pressure: 12 psi). The part of fermented primary liquid retained by the hollow fiber membrane of the column was called macromolecular isolated solution while the part passing through the hollow fiber membrane of the column was called small molecular isolated solution.

The small molecular isolated solution was added with 0.5% feather meal and incubated in a 50° C. constant temperature incubator for 48 hours at 150 rpm to increase the content of small molecular products to form a potency-boosted small molecular isolated solution. Afterwards, some water was removed from the potency-boosted small molecular isolated solution by vacuum concentration for concentration.

2. Enzyme Activity Analysis

The enzyme activity analysis was performed using azocasein assay. The formula of 0.5% azocasein solution is shown in Table 2.

TABLE 2

Formula of 0.5% azocasein solution

| Ingredient | Concentration (g/L) |
| --- | --- |
| $KH_2PO_4$ | 6.8 |
| $Na_2HPO_4$ | 7.1 |
| Azocasein | 1 |

200 μL of a solution to be tested with an appropriate concentration was added to 800 μL of 0.5% azocasein solution, and mixed uniformly to form a reaction solution, and then reacted at 65° C. After 30 minutes, 200 μL of 10% trichloroacetic acid (TCA) was immediately added to the reaction solution mentioned above to stop the reaction. After that, the reaction solution was centrifuged at 12,000×g at 4° C. for 10 minutes. Take 500 μL of the supernatant was taken and mixed with 500 μL of 0.2 M NaOH solution to form a mixture solution. $OD_{440}$ of this mixture solution was determined, and the enzyme activity of the solution to be tested was calculated based on a calibration curve of the concentration of the azocasein solution against the $OD_{440}$.

The calibration curve of the concentration of the azocasein solution against the $OD_{440}$ was plotted as described below. The azocasein solution was diluted by a serial half dilution method, and the $OD_{440}$ of each concentration was determined. A scatter diagram of the concentration of the azocasein solution against $OD_{440}$ was plotted, then add the trend line was added to obtain the equation of the concentration of the azocasein solution against OD440, and the $R^2$ value of the trend line was calculated. The $R^2$ value had to be greater than 0.995 and then the obtained the trend line was able to be used as the calibration curve. 1 unit (U) is defined as the decomposition of 1 μg of azocasein per minute, and the enzyme concentration is expressed in U/mL.

3. Analysis of Disulfide Bond Breaking Efficiency

A compound with a disulfide bond, 5,5'-disulfanediylbis (2-nitrobenzoic acid) (DTNB) will react with —SH which appears after breaking disulfide bonds of hair to produce 2-nitro-5-thiobenzoic acid (TNB) with yellow color. Therefore, the efficiency of breaking the disulfide bonds of hair (the content of —SH which appears after breaking the disulfide bonds of hair) of a sample to be tested can be evaluated by using DTNB and through the color reaction.

0.05 g of human hair was mixed with 5 mL of a sample to be tested to form a reaction solution and reacted at 60° C. for 30 minutes. After that, the reaction solution was filtered to remove the supernatant and 5 mL of DTNB buffer solution (0.002 M DTNB dissolved in 0.1 M phosphoric acid buffer solution (pH=8)) was added therein to react. After 5 minutes of reaction, the reaction solution was filtered to isolate the hair and the filtrate was analyzed at 412 nm to evaluate the production amount of TNB, and the efficiency of breaking the disulfide bonds of hair of the sample to be tested was evaluated thereby.

4. Reduction Activity Analysis

Red prussiate can be reduced to yellow prussiate, and yellow prussiate can form Prussian blue by $Fe^{3+}$. Therefore, reduction activity of a sample to be tested can be determined using red prussiate and $Fe^{3+}$.

0.3 mL of sample (experimental group) or distilled water (blank group) was mixed with 0.3 mL of 0.2 M potassium phosphate buffer (pH 6.6) and 0.3 mL of 1% red prussiate aqueous solution to form a mixture solution and placed in a 50° C. water bath for 20 minutes. After the mixture was cooled to room temperature, 10% trichloroacetic acid aqueous solution was added to the mixture solution and centrifuged at 3000 rpm for 20 minutes. 1.2 mL of supernatant was taken and added with 1.2 mL of distilled water and uniformly mixed with 0.24 mL of 0.1% ferric chloride to form a reaction solution. The reaction solution was then allowed to stand for 10 min to detect the absorbance value of $OD_{700}$ to evaluate the production amount of Prussian blue which was used as an indicator of the reduction activity.

The reduction activity is set to the reading value of $OD_{700}$ of the sample minus the reading value of $OD_{700}$ of the blank group.

5. Skin Irritation Analysis

Skin irritation analysis of the samples to be tested was performed by keratinocytes according to OECD439 (In Vitro Skin Irritation: Reconstructed Human Epidermis Test Method).

The EpiDerm™ bionic skin was placed in assay medium (EPI-100-NMM) and then placed in a 37° C., 5% $CO_2$ cell incubator to incubate for 60±5 minutes. Next, the bionic skin was moved in new assay medium and placed in a 37° C., 5% $CO_2$ cell incubator to incubate overnight (18±3 hours). A substance to be tested (25 mg solid or 30 μL liquid) was added to the bionic skin, and then the bionic skin was placed in a 37° C., 5% $CO_2$ cell incubator to incubate. After about 35±1 minutes, the bionic skin mentioned above was taken and placed on a laminar airflow bench until the substance to be tested as whole was in contact with the bionic skin for 60±1 minutes. Next, the substance to be tested was washed off the bionic skin with DPBS.

Afterwards, the bionic skin mentioned above was placed in assay medium and incubated in a 37° C., 5% $CO_2$ cell incubator for 24±2 hours, and then the assay medium was exchanged and the bionic skin was placed in a 37° C., 5% $CO_2$ cell incubator again to incubate for 18±2 hours.

After that, the bionic skin was incubated with 1 mg/mL MTT solution for 3 hours±5 minutes in a 37° C., 5% $CO_2$ cell incubator, and then the bionic skin was washed with DPBS.

Finally, the purple crystals were dissolved with isopropanol and the survival rate was calculated by the reading value of $OD_{570}$. If the survival rate was <50%, the substance to be tested was considered to be skin irritant.

6. Skin Sensitization Analysis

Skin sensitization analysis of the samples to be tested was performed by keratinocytes according to OECD442D (In Vitro Skin Sensitisation-ARE-Nrf2 Luciferase Test Method).

2-fold dilution was performed on a substance to be tested from a maximum concentration of 400 ng/mL with 1% DMSO aqueous solution. Different concentrations of the substance to be tested were then added to KeratinoSens™ cells and incubated for 48 hours in a 37° C., 5% $CO_2$ cell incubator.

Cells were subsequently assayed for intracellular Nrf2 activity using the Luciferase Assay System (Promega, E1501), and cell viability was detected using the MTT method. If the Nrf2 induction proportion was greater than 1.5 times when the cell viability was greater than 70%, the substance to be tested was considered to be skin sensitizing.

7. Eye Irritation Assessment

The eye irritation analysis of a sample to be tested was performed by rabbit corneal cells according to the OECD491 (Short Time Exposure In Vitro Test Method for Identifying i) Chemicals Inducing Serious Eye Damage and ii) Chemicals Not Requiring Classification for Eye Irritation or Serious Eye Damage).

The sample to be tested was adjusted to concentrations of 5% and 0.05% with physiological saline, and then added to SIRC cells. After standing at room temperature for 5 minutes, the cells were washed twice with PBS. After that, the cells were added to a medium containing 0.5 mg/mL MTT and cultured in a 37° C., 5% $CO_2$ cell incubator for 2 hours.

Finally, the purple crystals were dissolved with 0.04 N hydrochloric acid-isopropanol, and the survival rate was calculated using the reading value of $OD_{570}$. If the survival rate of 0.5% and 0.05% the sample to be tested was greater than 70%, the sample to be tested was considered belonging to No Category (no need to classify eye irritation and serious eye damage). If the survival rate of 0.5% and 0.05% the sample to be tested was less than or equal to 70%, the sample to be tested was considered belonging to Category 1 (causing serious eye damage).

8. Stability Analysis

A sample to be tested was added or not added with preservatives, and sampled at each time point to analyze the enzyme activity to confirm its stability.

The fermented primary liquid prepared by the method mentioned above was used as the sample to be tested. The fermented primary liquid added with respective preservatives were used as 3 experimental groups while the fermented primary liquid without addition of preservative was used as a control group. The preservatives used in the 3 experimental groups were 0.3% chlorphenesin, 1% para-hydroxyacetophenone, and a mixture of 0.2% chlorphenesin and 0.6% para-hydroxyacetophenone, respectively. The 3 experimental groups and the control group were aseptically packaged and stored at 25° C., and then sampled at specific time points and analyzed for enzyme activity according to the foregoing method. The specific time points were the day of packaging and 1, 2, 3, 7, 10, 14, 17, 21, 28, 35, 42, 49 and 56 days after packaging.

9. Preparation of Plant-Derived Extracts as Alkali Agents

A plant or plant source substrate was ground to obtain a powder. The powder was mixed with water at a weight ratio of powder to water of 1:10 and extracted by ultra-sonication for 1 hour to obtain a crude extract. The crude extract was then filtered through a 0.8 μm membrane to remove excess impurities, and the resulting filtrate was used as a plant-derived alkali agent.

Moreover, the above plant-derived alkali agent could be further concentrated under reduced pressure at 50° C.

B. Experimental Results

1. Example 1

Analysis of Fermented Primary Liquid (1) Optimization of Enzyme Reaction Conditions for Fermented Primary Liquid (i) Reaction Temperature The fermented primary liquid produced by *Bacillus licheniformis* GI_5E-1 was subjected to the enzymatic activity analysis described in the above experimental methods, and from 30° C. to 80° C., an enzymatic activity determination was performed every 10° C.

The results are shown in FIG. 1.

According to FIG. 1, it is known that the fermented primary liquid produced by *Bacillus licheniformis* GI_5E-1 has excellent enzymatic activity at all temperatures and has the best enzymatic activity at 60° C. ($OD_{440}$=1.9 (enzyme content 939 U/mL)).

(ii) Reaction pH

Reaction pH for the fermented primary liquid produced by *Bacillus licheniformis* GI_5E-1 was adjusted through adjusting pH value of 50 mM phosphate buffer solution for preparing 0.5% azocasein solution from pH 4 to pH 11 according to the experimental method described above, and an enzyme activity determination was performed every one pH.

Figure 2:
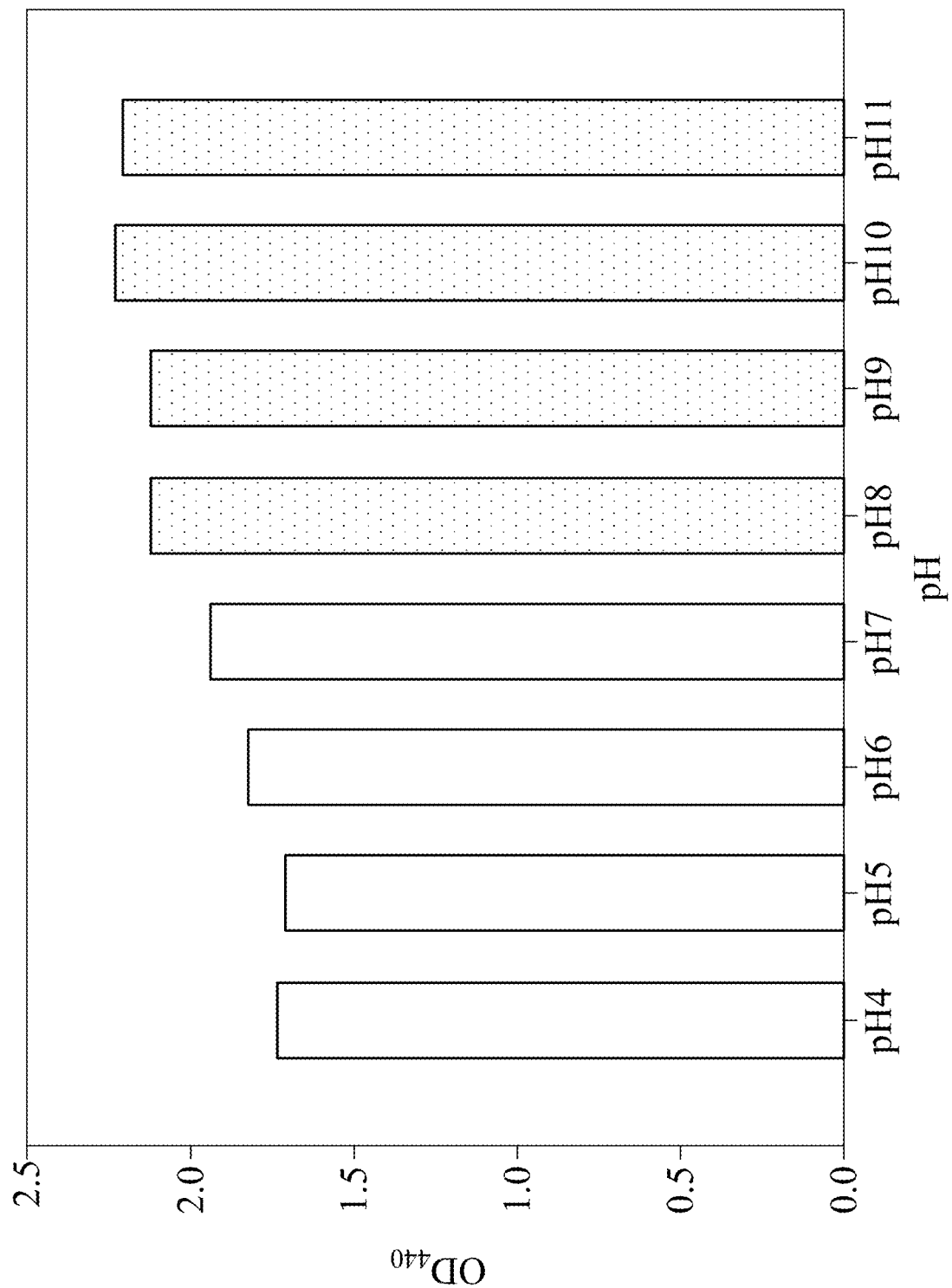
FIG. 2 shows the enzymatic activities of the fermented primary liquid produced by *Bacillus licheniformis* GI_5E-1 at different pH values.

The experimental results are shown in FIG. 2.

According to FIG. 2, it is known that the fermented primary liquid produced by *Bacillus licheniformis* GI-5E-1 has excellent enzyme activity at each pH, and has better enzyme activity in an alkaline environment (pH 8 to pH 11).

(2) Disulfide Bond Breaking Efficiency of Fermented Primary Liquid

The fermented primary liquid produced by *Bacillus licheniformis* GI_5E-1 was subjected to the analysis of disulfide bond breaking efficiency described in the experimental method mentioned above, and the reaction temperature was set to 60° C. or 90° C. to perform the analysis of disulfide bond breaking efficiency for the fermented primary liquid.

Figure 3:
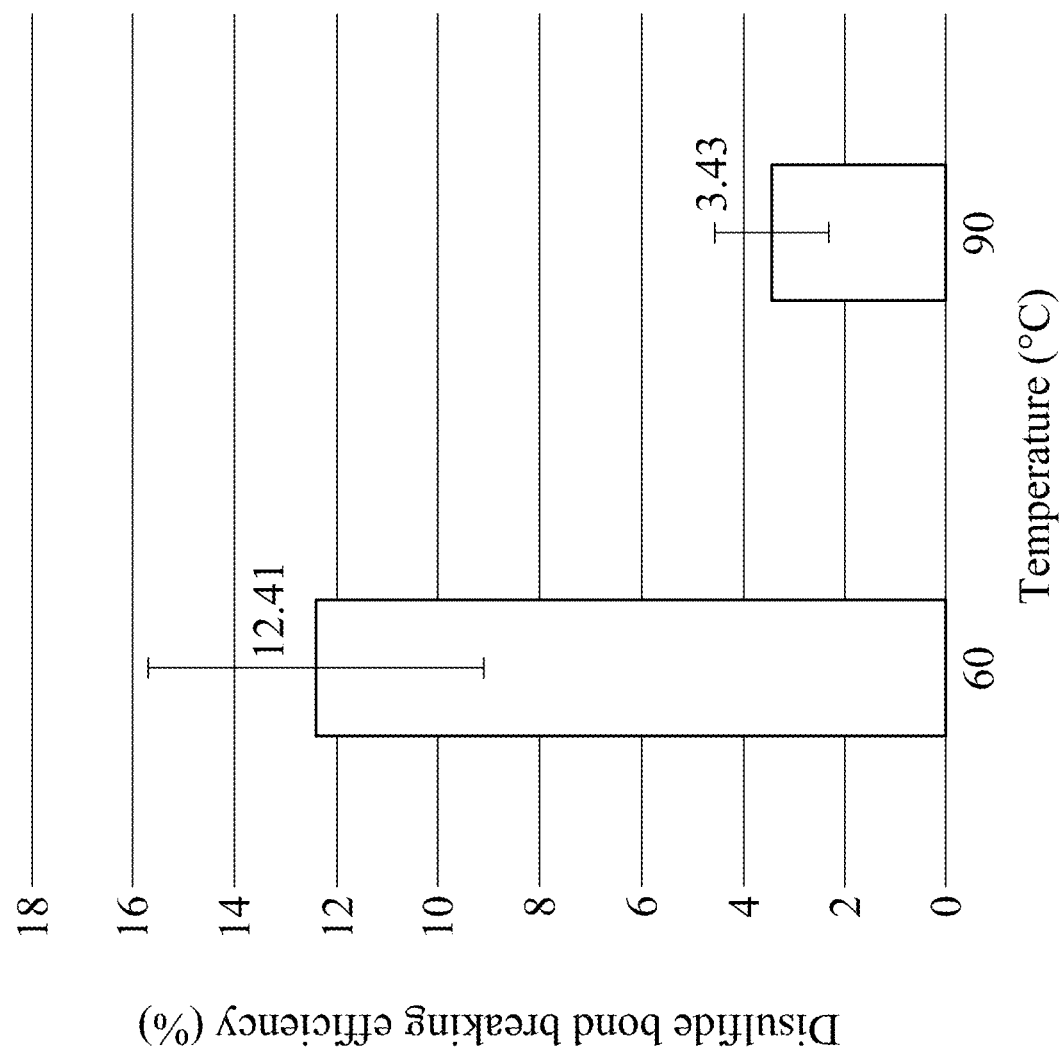
FIG. 3 shows the disulfide bond breaking efficiencies of the fermented primary liquid produced by *Bacillus licheniformis* GI_5E-1 at different temperatures.

The results are shown in FIG. 3.

According to FIG. 3, it is known that the fermented primary liquid has disulfide bond breaking ability at both 60° C. and 90° C. Moreover, compared to at 90° C., the fermented primary liquid has better disulfide bond breaking efficiency at 60° C. (3.43% vs. 12.41%).

(3) Analysis of Disulfide Bond Breaking Efficiency and Reduction Activity of Fermented Primary Liquid Produced by Different Strains The fermented primary liquid produced by commercially available *Bacillus licheniformis* BCRC 14353 or the fermented primary liquid produced by *Bacillus licheniformis* GI_5E-1 was subjected to the analysis of disulfide bond breaking efficiency described in the experimental method mentioned above, wherein the reaction temperature was adjusted from 60° C. to 30° C. or 50° C. to evaluate the disulfide bond breaking efficiency of the fermented primary liquid.

In addition, the fermented primary liquid produced by *Bacillus licheniformis* BCRC 14353 or the fermented primary liquid produced by *Bacillus licheniformis* GI_5E-1 was subjected to the reduction activity analysis described in the experimental method mentioned above, in which the reaction temperature was set to 30° C. or 50° C. to evaluate the reduction activity of the fermented primary liquid.

Figure 4:
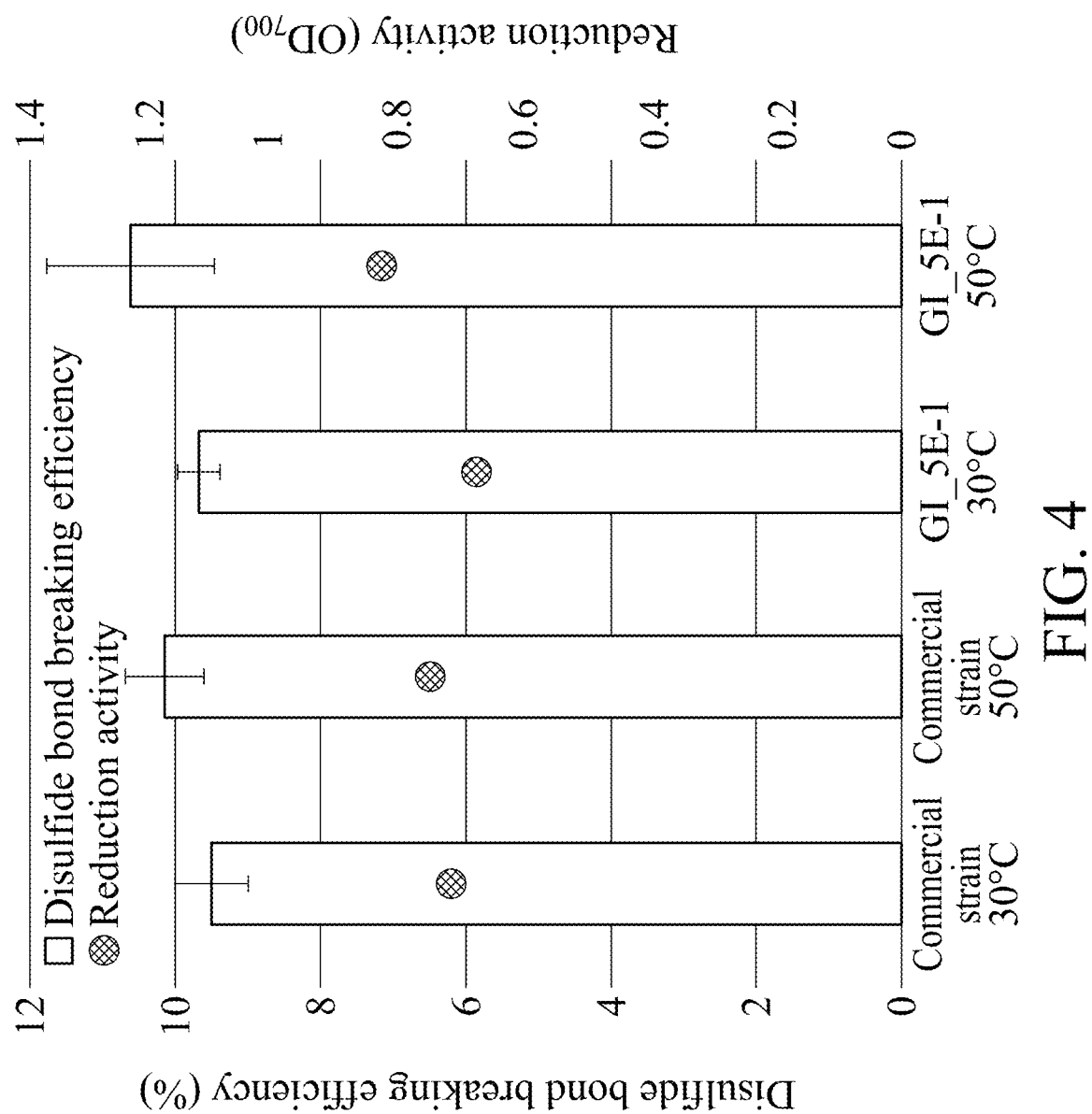
FIG. 4 shows the disulfide bond breaking efficiency and reduction activity of the fermented primary liquid produced by *Bacillus licheniformis* BCRC 14353 or the fermented primary liquid produced by *Bacillus licheniformis* GI_5E-1.

The results are shown in FIG. 4.

According to FIG. 4, it is known that the fermented primary liquid produced by *Bacillus licheniformis* BCRC 14353 has disulfide bond breaking ability and reduction activity at both of 30° C. and 50° C., and similarly, the fermented primary liquid produced by *Bacillus licheniformis* GI_5E-1 also has disulfide bond breaking ability and reduction activity at both of 30° C. and 50° C.

Moreover, the disulfide bond breaking efficiency of the fermented primary liquid produced by *Bacillus licheniformis* GI_5E-1 is better than that of the fermented primary liquid produced by *Bacillus licheniformis* BCRC 14353 whether at 30° C. or 50° C.

(4) Skin Irritation Analysis of Fermented Primary Liquid

The fermented primary liquid produced by *Bacillus licheniformis* GI_5E-1 was subjected to the skin irritation analysis described in the experimental methods mentioned above.

Figure 5:
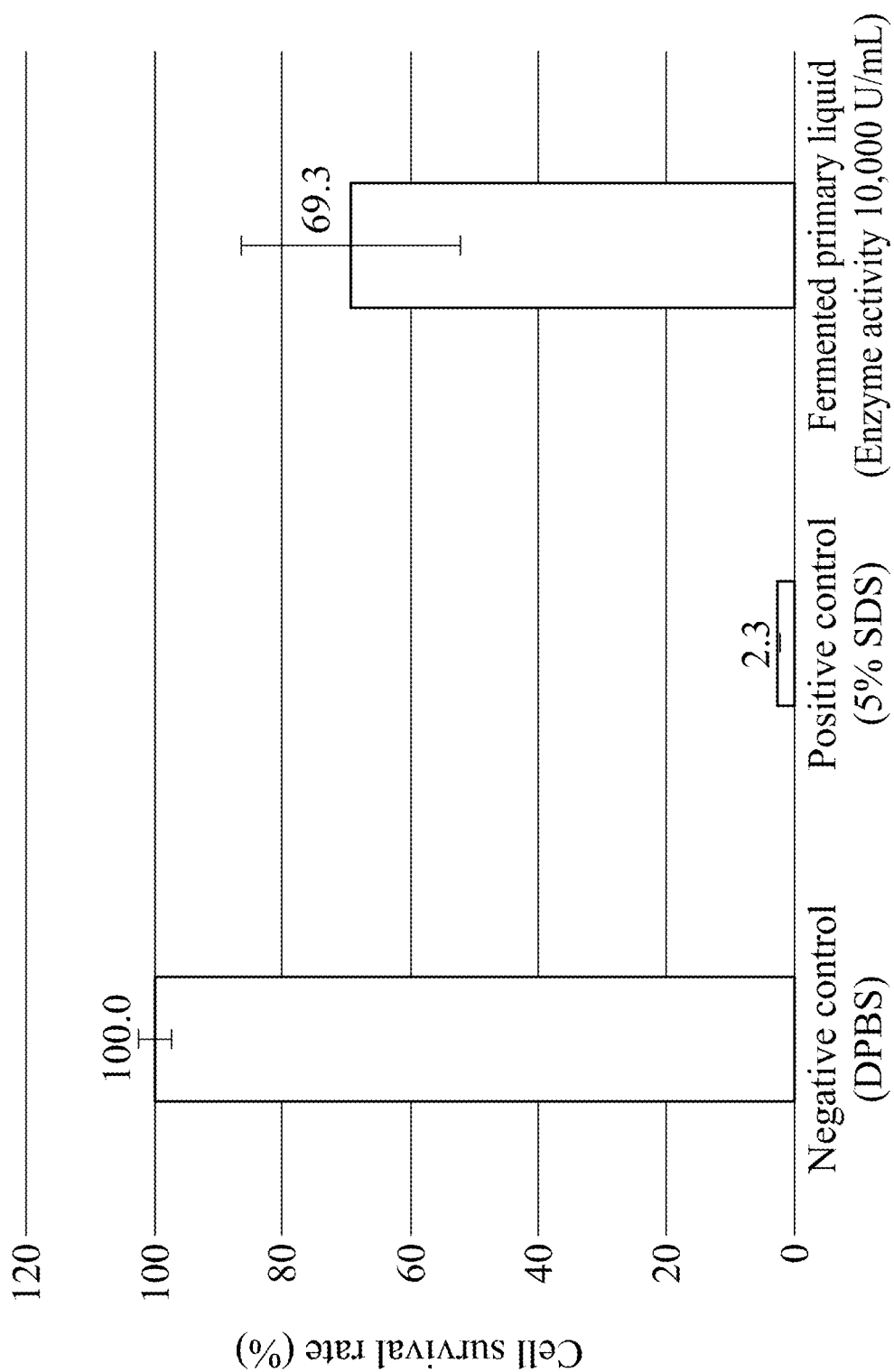
FIG. 5 shows the results of skin irritation analysis of the fermented primary liquid produced by *Bacillus licheniformis* GI_5E-1.

The results are shown in FIG. 5.

According to FIG. 5, it is known that the cell survival rate of stratum corneum cells treated with the fermented primary liquid produced by *Bacillus licheniformis* GI-5E-1 was 69.3%. Specifically, based on the OECD439 guideline, the cell survival rate of the cells treated with a sample to be tested is greater than 50%, which means that the sample to be tested has no skin irritation. Therefore, the fermented primary liquid produced by *Bacillus licheniformis* GI_5E-1 is regarded as no skin irritation.

(5) Skin Sensitization Analysis of Fermented Primary Liquid

The fermented primary liquid produced by *Bacillus licheniformis* GI_5E-1 is diluted to produce different concentrations of solutions to be tested and the different concentrations of solutions to be tested are subjected to the skin sensitization analysis described in the experimental methods mentioned above.

Figure 6:
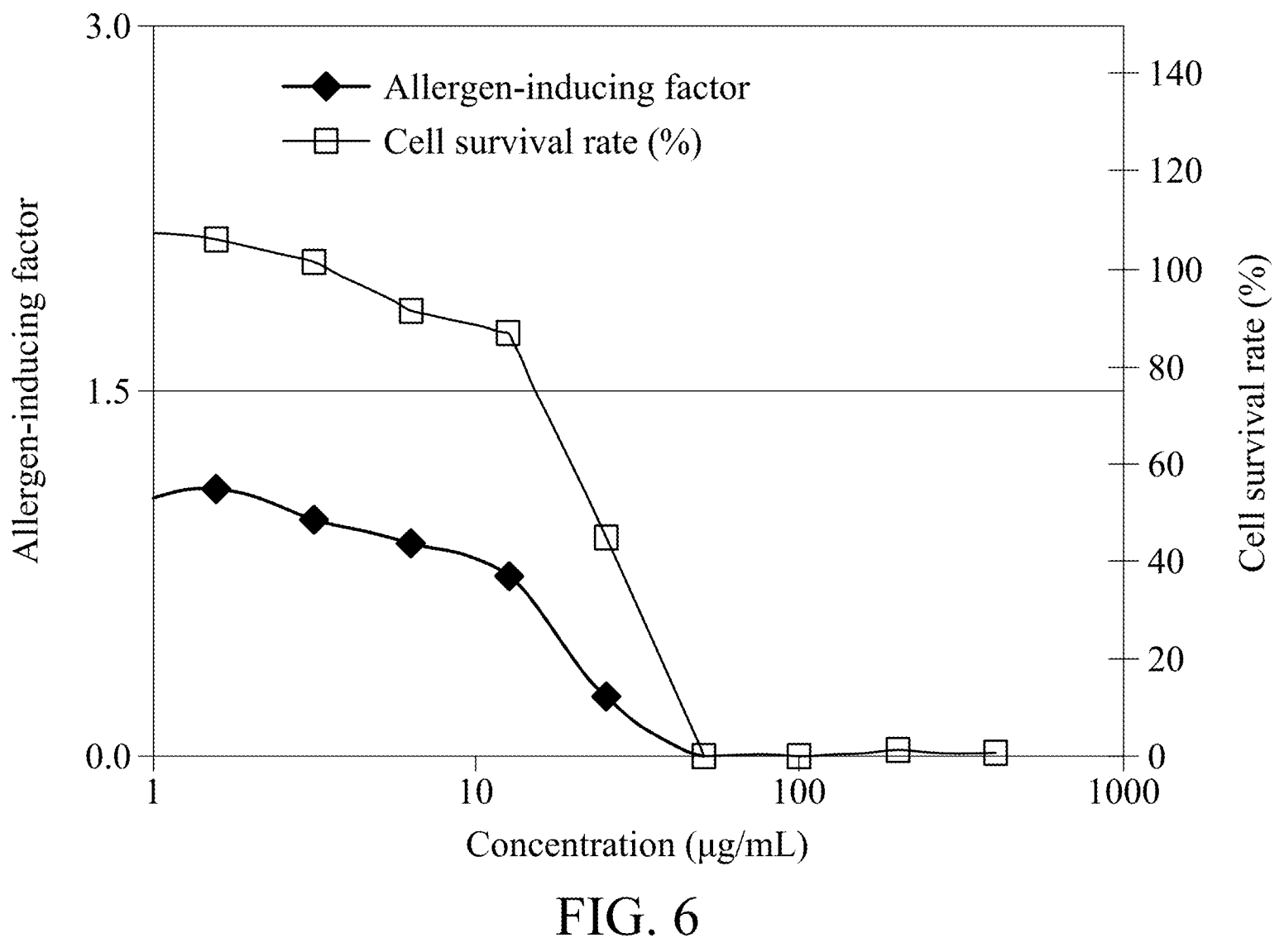

The results are shown in FIG. 6.

According to FIG. 6, it is known that the cell survival rates of stratum corneum cells treated with different concentrations of solutions to be tested are greater than 70%, and the allergen-inducing factors produced by the stratum corneum cells treated with different concentrations of solutions to be tested are all less than 1.5.

Specifically, based on the OECD442D guideline, the cell survival rate of the cells treated with a sample to be tested is greater than 70% or the allergen-inducing factor produced by the cells treated with a sample to be tested is less than 1.5, which means that the sample to be tested has no skin sensitization. Therefore, the fermented primary liquid produced by *Bacillus licheniformis* GI_5E-1 is regarded as no skin sensitization.

(6) Eye Irritation Analysis of Fermented Primary Liquid

The fermented primary liquid produced by *Bacillus licheniformis* GI_5E-1 was diluted to produce different enzyme activities of solutions to be tested, and the different enzyme activities of solutions to be tested are subjected to the eye irritation analysis described in the experimental methods mentioned above.

Figure 7:
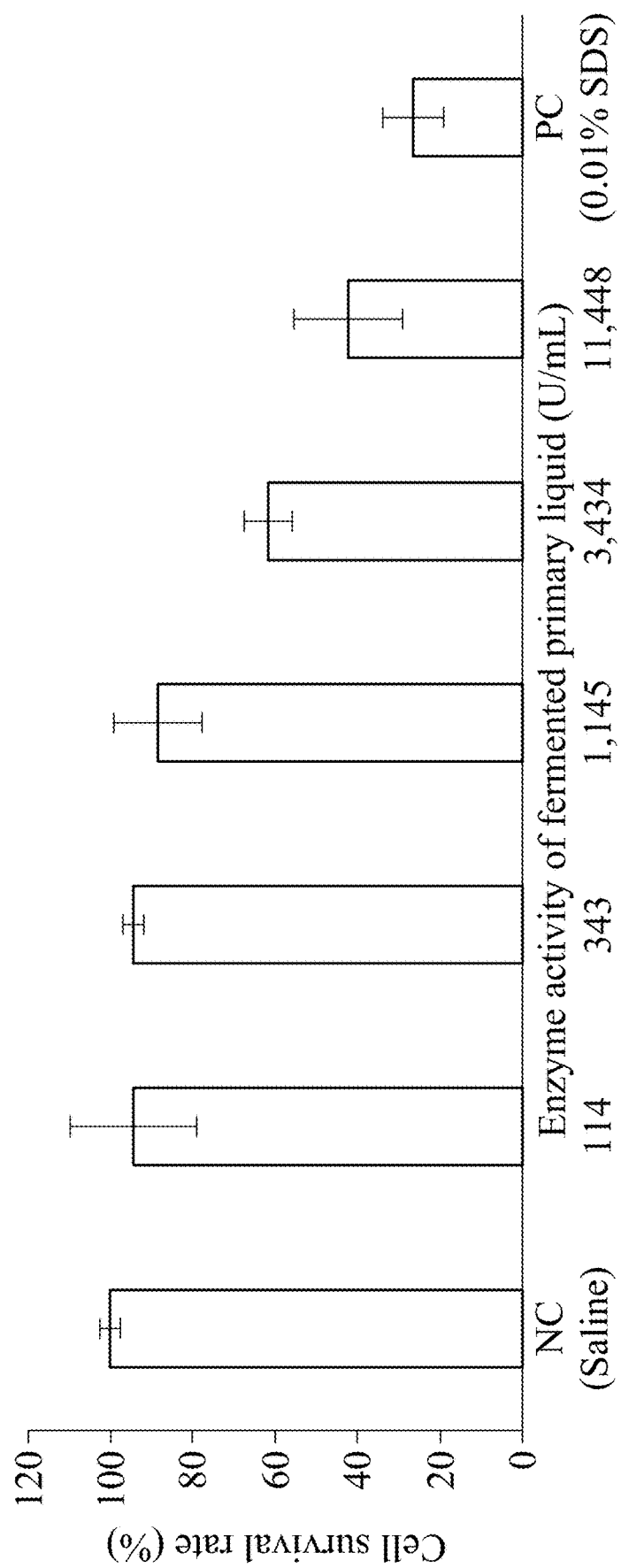
FIG. 7 shows the results of the eye irritation analysis of the fermented primary liquid generated by *Bacillus licheniformis* GI_5E-1.

The results are shown in FIG. 7.

According to FIG. 7, it is known that the cell survival rates of rabbit corneal cells treated with the solutions to be tested with enzyme activities of below 3,000 U/mL are all greater than 70%. Specifically, based on the OECD491 guideline, the cell survival rate of the cells treated with a sample to be tested is greater than 70%, which means that the sample to be tested has no eye irritation. Therefore, when the fermented primary liquid produced by *Bacillus licheniformis* GI_5E-1 is diluted to an enzyme activity of 3,000 U/mL or less, it is considered no eye irritation.

(7) Stability Analysis of Fermented Primary Liquid

The fermented primary liquid produced by *Bacillus licheniformis* GI_5E-1 was subjected to the stability analysis described in the experimental methods mentioned above.

Figure 8:
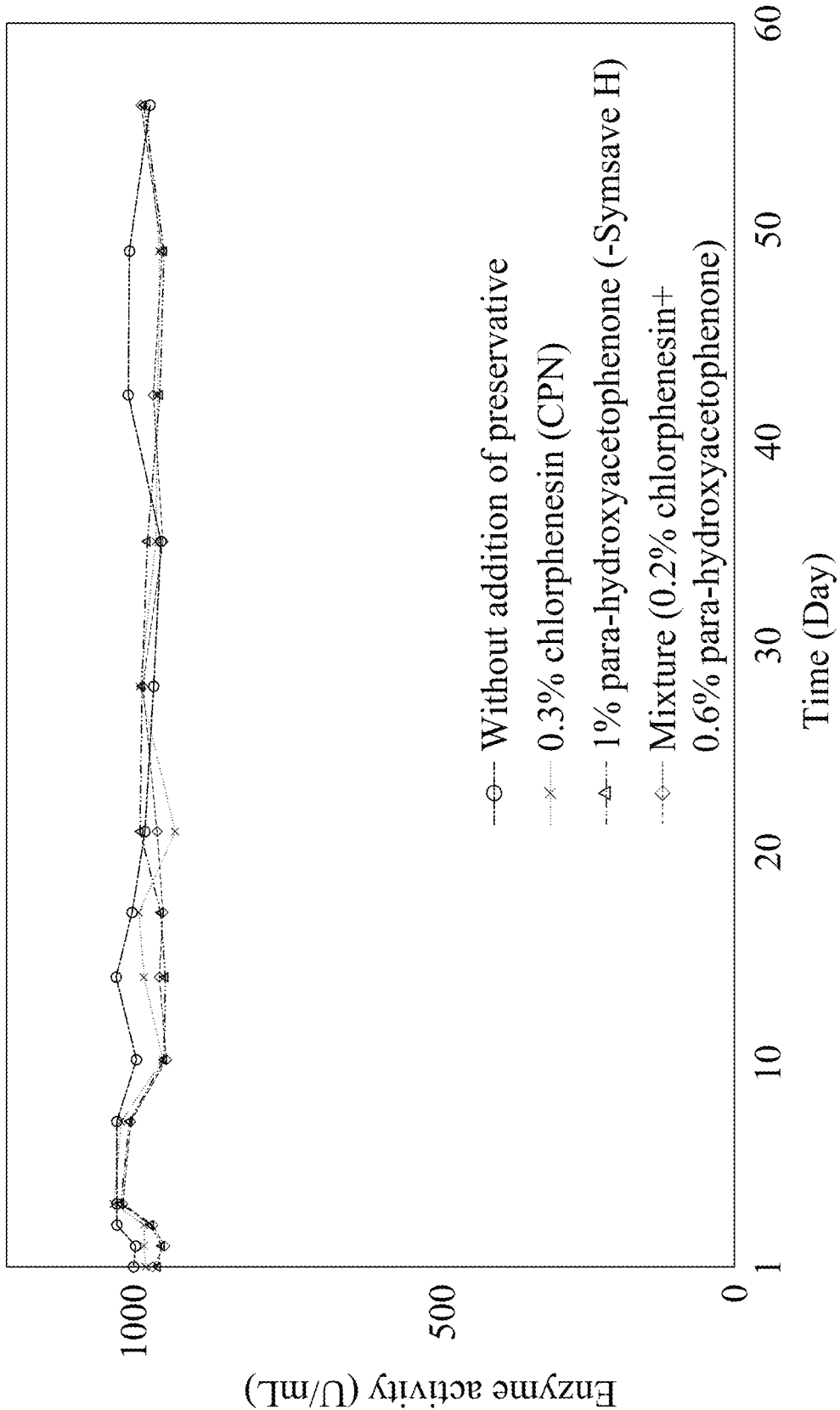
FIG. 8 shows the results of stability analysis of the fermented primary liquid produced by *Bacillus licheniformis* GI_5E-1.

The results are shown in FIG. 8.

Based on FIG. 8, it is know that with or without addition of preservative, the fermented primary liquid produced by *Bacillus licheniformis* GI-5E-1 can maintain good enzyme activity within 55 days, and the enzyme activity is not significantly reduced. Namely, the fermented primary liquid produced by *Bacillus licheniformis* GI_5E-1 can maintain excellent stability without addition of preservative.

Example 2

Analysis of Macromolecular Isolated Solution

The macromolecular isolated solution of the fermented primary liquid produced by *Bacillus licheniformis* GI_5E-1 was subjected to electrophoresis analysis.

Figure 9:
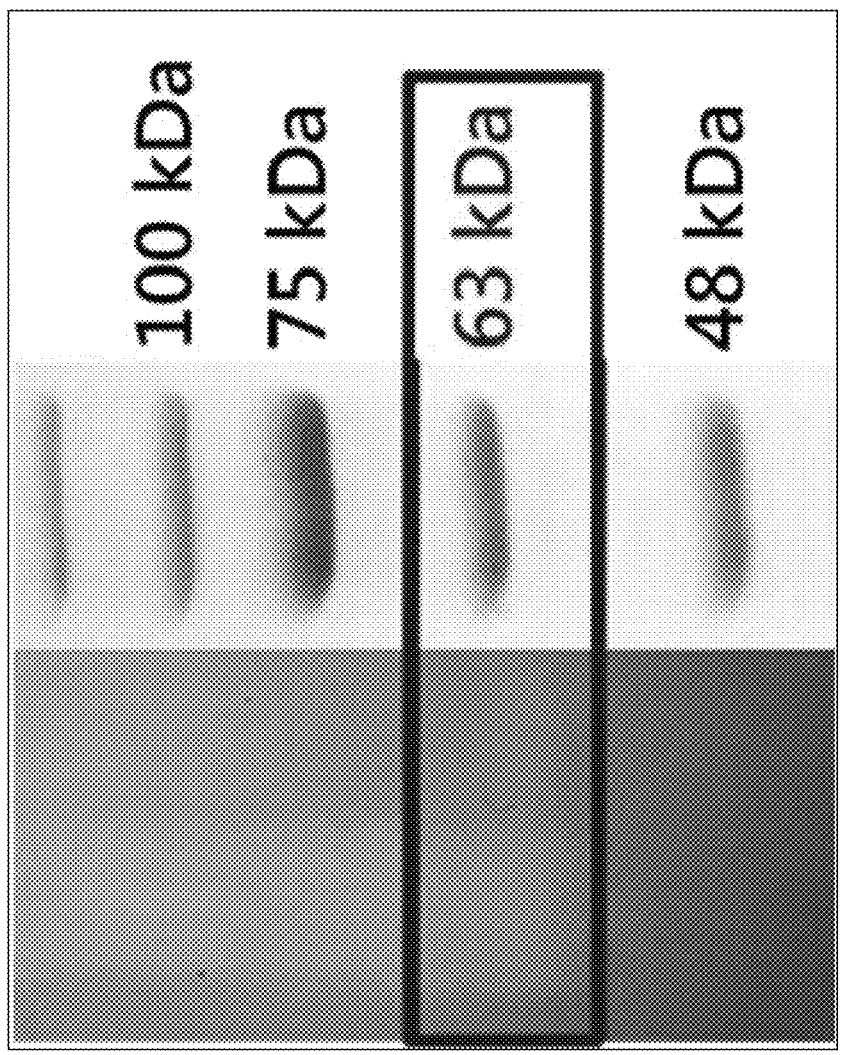
FIG. 9 shows the result of electrophoretic analysis of the macromolecular isolated solution of the fermented primary liquid generated by *Bacillus licheniformis* GI_5E-1.

The results are shown in FIG. 9.

According to FIG. 9, it is know that the macromolecular isolated solution of the fermented primary liquid produced by *Bacillus licheniformis* GI_5E-1 has a protein with a molecular weight of 63 kDa.

After the protein was taken from the electrophoresis gel, ENERGENESIS BIOMEDICAL CO., LTD. was entrusted to perform protein identification with Proteome Discoverer V2.2.0.388 software.

The results are shown in Table 3.

TABLE 3

| | Description for protein | Score |
|---|---|---|
| G9JKM6 | Alkaline protease<br>OS = *Bacillus licheniformis*<br>OX = 1402 PE = 4 SV = 1 | 117 |
| A0A0G2UQ23 | Keratinase<br>OS = *Bacillus licheniformis*<br>OX = 1402 PE = 3 SV = 1 | 117 |
| A0A415JD23 | Glutamate-1-semialdehyde<br>2,1-aminomutase<br>OX = 1402 GN = hemL PE = 3 SV = 1 | 82 |

According to Table 3, it is known that the protein with a molecular weight of 63 kDa contained by the macromolecular isolated solution of the fermented primary liquid produced by *Bacillus licheniformis* GI_5E-1 may be an alkaline protease or keratinase which have higher identification scores.

Example 3

Analysis of Potency-Boosted Small Molecular Isolated Solution

1. Component identification of potency-boosted small molecular isolated solution ENERGENESIS BIOMEDICAL CO., LTD. was entrusted to identify the peptides in the components of the potency-boosted small molecular isolated solution of the fermented primary liquid produced by *Bacillus licheniformis* GI_5E-1 by Proteome Discoverer V2.2.0.388 software.

The identification results are shown in Table 4.

TABLE 4

| Item | Sequence of peptide | Score |
|---|---|---|
| 1 | FTQAGSEVSALLGR<br>(SEQ ID NO. 1) | 94 |
| 2 | VNVADcGAEALAR<br>(SEQ ID NO. 2) | 92 |
| 3 | DVALSSGSAcTSASLEPSYVLR<br>(SEQ ID NO. 3) | 85 |
| 4 | WELLQQQGPSGPR<br>(SEQ ID NO. 4) | 82 |
| 5 | QSVEADINGLR<br>(SEQ ID NO. 5) | 80 |
| 6 | VGYAVcQINLGLSQR<br>(SEQ ID NO. 6) | 79 |
| 7 | SLDLDSIIAEVK<br>(SEQ ID NO. 7) | 79 |
| 8 | LISGEHVGALAMSEPNAGSDVVSMK<br>(SEQ ID NO. 8) | 75 |
| 9 | VGALTDEINFLR<br>(SEQ ID NO. 9) | 73 |
| 10 | LcYVALDFEQEMATAASSSSLEK<br>(SEQ ID NO. 10) | 67 |

Based on Table 4, it is known that there are 10 peptides with different sequences in the small molecular isolated solution.

2. Reduction Activity Analysis for Peptides

ENERGENESIS BIOMEDICAL CO., LTD. was entrusted to synthesize the 10 peptides mentioned above. After that, the 10 synthesized peptides were subjected to the reduction activity analysis described in the experimental methods mentioned above to evaluate their reduction activity.

Figure 10:
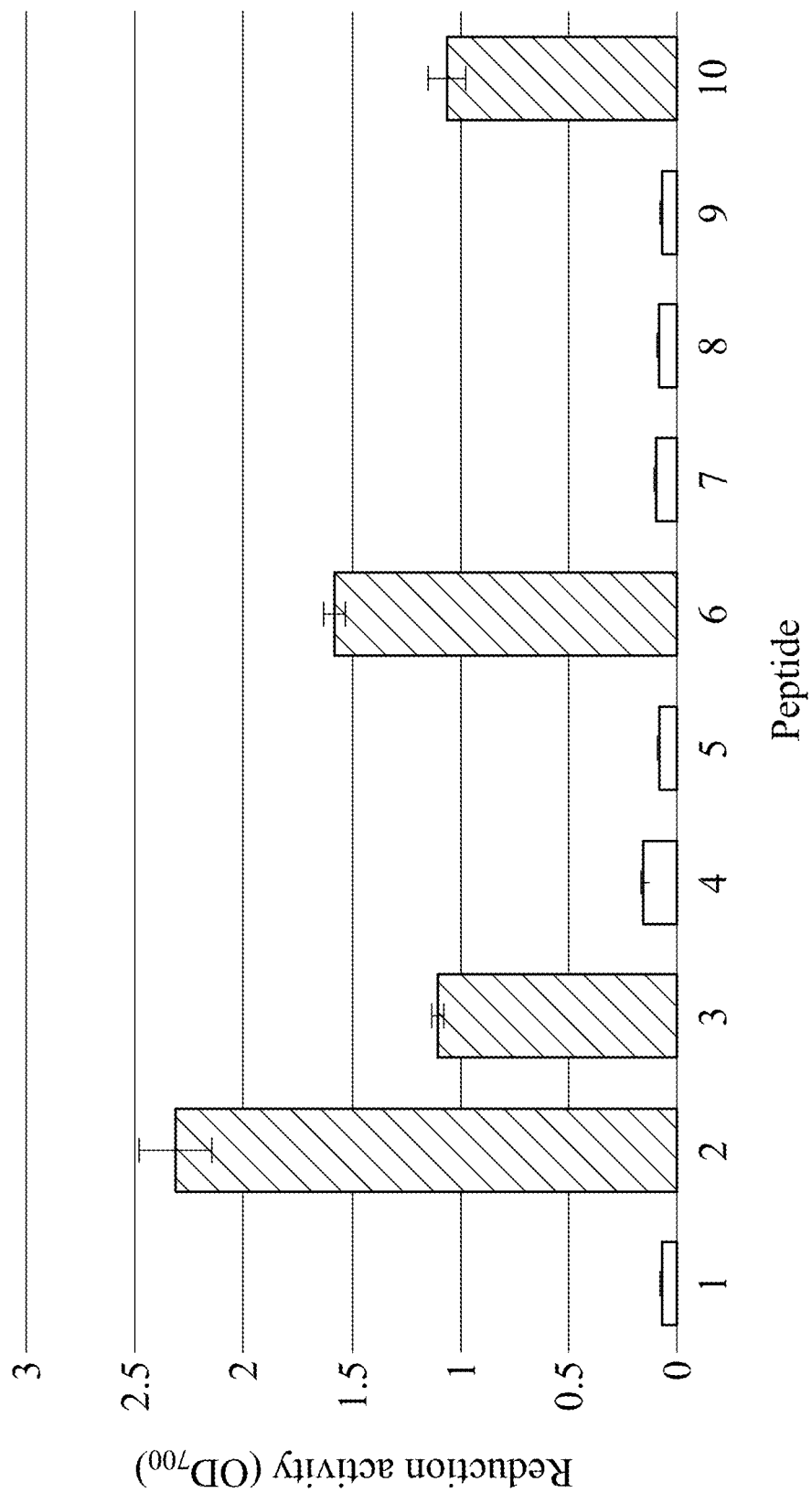
FIG. 10 shows the reducing capacities of 10 peptides contained in the small molecular isolated solution of the fermented primary liquid generated by *Bacillus licheniformis* GI_5E-1.

The results are shown in FIG. 10.

According to FIG. 10, it is known that the 10 peptides mentioned above all have reduction activity, wherein Peptide 2, Peptide 3, Peptide 6, and Peptide 10 have higher reduction activity.

Example 4

Analysis of Plant-Derived Extracts as Alkali Agents

1. Analysis of Disulfide Bond Breaking Efficiency of Fermented Primary Liquid Combined with Different Plant-Derived Extracts The tea stems, mulberry leaves and coffee grounds were subjected the preparation of plant-derived extracts as alkali agents as described in the experimental methods mentioned above to obtain a water extract of tea stems (containing theophylline), a water extract of mulberry leaves (containing plant alkaloids) and a water extract of coffee grounds (containing nicotine).

The foregoing extracts and the fermented primary liquid produced by *Bacillus licheniformis* GI_5E-1 were mixed at a volume ratio of 1:1 to form a mixture, and the mixture was subjected to the analysis of disulfide bond breaking efficiency described in the experimental methods mentioned above.

Figure 11:
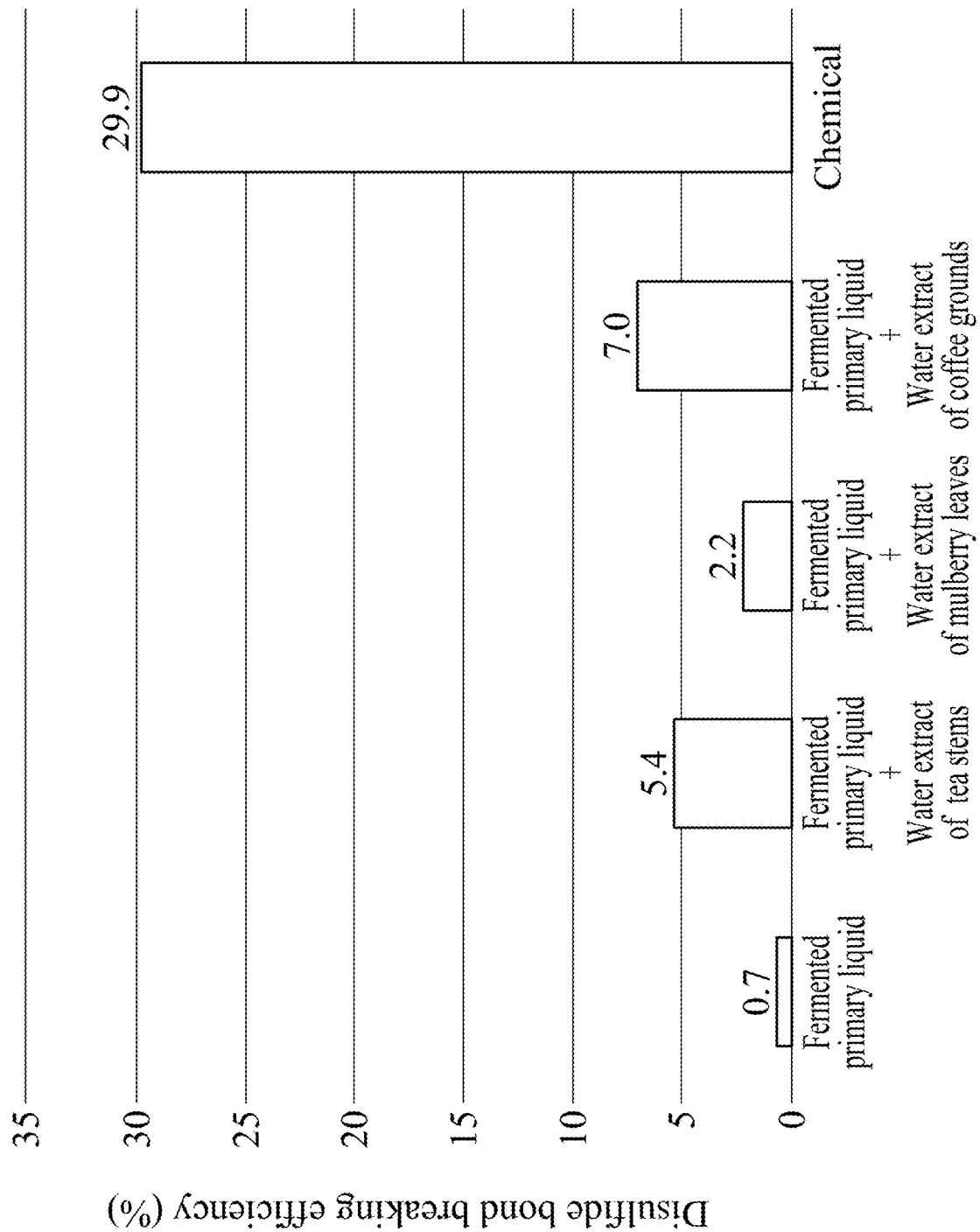
FIG. 11 shows the disulfide bond breaking efficiency of a mixture of a water extract of tea stems, a water extract of mulberry leaf or a water extract of coffee grounds and the fermented primary liquid produced by *Bacillus licheniformis* GI_5E-1.

The results are shown in FIG. 11.

Based on FIG. 11, it is known that after the fermented primary liquid is combined with the respective plant-derived extracts mentioned above, the disulfide bond breaking efficiency of the fermented primary liquid is significantly improved, wherein using the water extract of coffee grounds as an alkali agent to assist the fermented primary liquid can increase the disulfide bond breaking efficiency of the fermented primary liquid to 10 times. In addition, the water extract of coffee grounds can also absorb the original special smell of the fermented primary liquid.

2. Effect of Concentration of Alkali Agent on Disulfide Bond Breaking Efficiency of Fermented Primary Liquid The foregoing water extract of coffee grounds was used as an alkali agent and added to the fermented primary liquid produced by *Bacillus licheniformis* GI_5E-1 at a concentration of 10% (v/v), 30% (v/v) or 50% (v/v) to form a mixture, and the mixture was subjected to the disulfide bond breaking efficiency analysis described in the experimental methods above.

Figure 12:
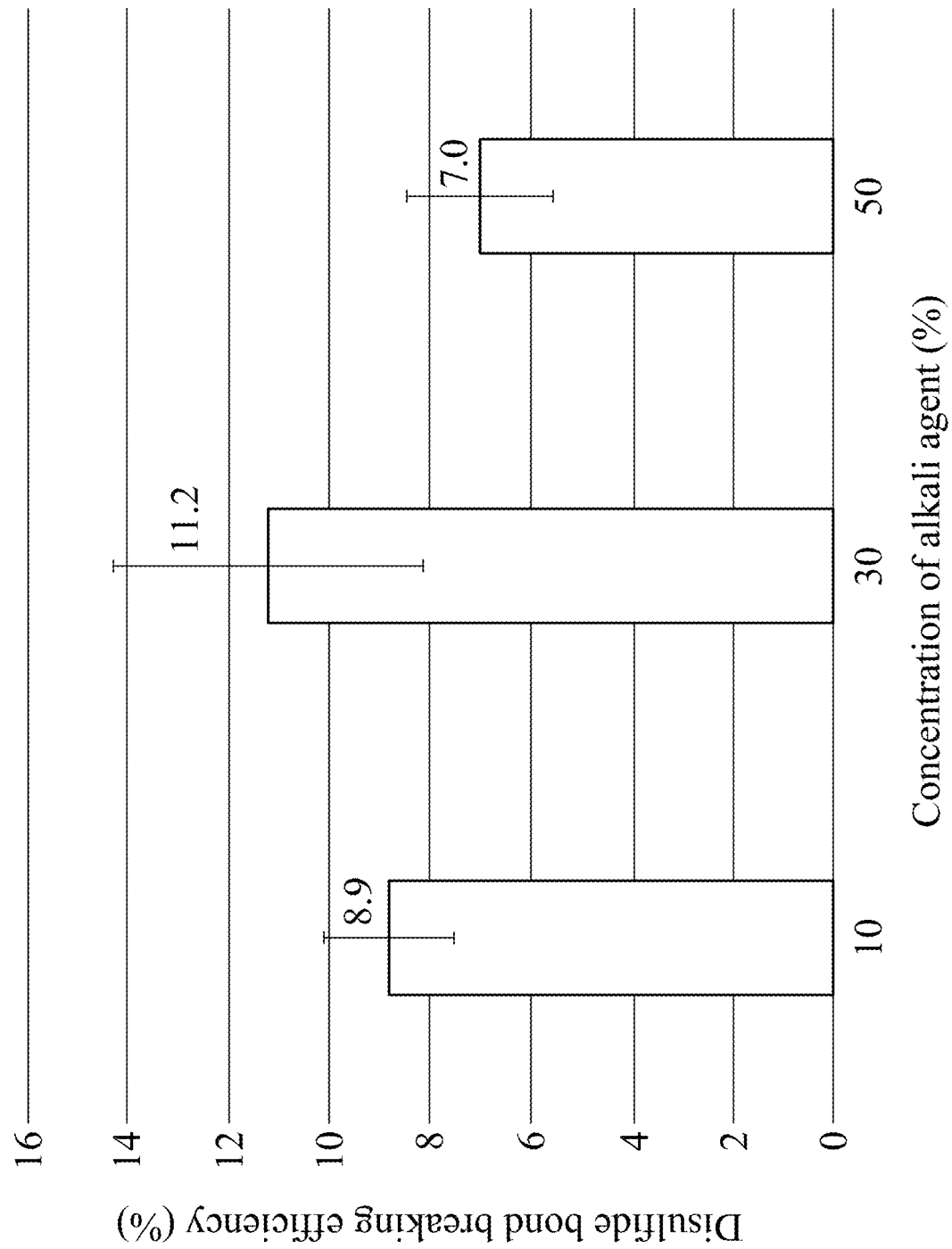
FIG. 12 shows the disulfide bond breaking efficiencies of the mixtures of a water extract of coffee grounds at different addition amount and the fermented primary liquid produced by *Bacillus licheniformis* GI_5E-1.

The results are shown in FIG. 12.

According to FIG. 12, it is known that the fermented primary liquid has the highest disulfide bond breaking efficiency of 11.2% at a concentration of alkali agent of 30%, and compared to at a concentration of alkali agent of 10%, increase in disulfide bond breaking efficiency of the fermented primary liquid is about 26% at a concentration of alkali agent of 30%.

Example 5

Analysis of Disulfide Bond Breaking Efficiency of Different Formulations of Hair Shape Change Compositions The macromolecular isolated solution and the enhanced small molecular isolated solution of the fermented primary liquid produced by *Bacillus licheniformis* GI_5E-1 were diluted to adjust the enzyme activity and reducing power, respectively. After that, the respective macromolecular isolated solutions and the respective potency-boosted small molecular isolated solutions were combined, and mixed with 30% (v/v) water extract of coffee grounds in a volume ratio of 1:1 to prepare the following 5 samples of hair shape change compositions with different formulas.

(i) Sample S1: Containing 33.3% (v/v) of macromolecular isolated solution, 11% (v/v) of small molecular isolated solution, 15% (v/v) of water extract of coffee grounds and 40.7% (v/v) of pure water;

(ii) Sample S2: Containing 21.5% (v/v) of macromolecular isolated solution, 9% (v/v) of small molecular isolated solution, 15% (v/v) of water extract of coffee grounds and 54.5% (v/v) of pure water;

(iii) Sample S3: Containing 21.5% (v/v) of macromolecular isolated solution, 14% (v/v) of small molecular isolated solution, 15% (v/v) of water extract of coffee grounds and 49.5% (v/v) of pure water;

(iv) Sample S4: Containing 21.5% (v/v) of macromolecular isolated solution, 18% (v/v) of small molecular isolated solution, 15% (v/v) of water extract coffee grounds and 45.5% (v/v) of pure water;

(v) Sample S5: Containing 21.5% (v/v) of macromolecular isolated solution, 21% (v/v) of small molecular isolated solution, 15% (v/v) of water extract of coffee grounds and 42.5% (v/v) of pure water.

The 5 samples were subjected to the analysis of the disulfide bond breaking efficiency described in the experimental methods mentioned above.

Figure 13:
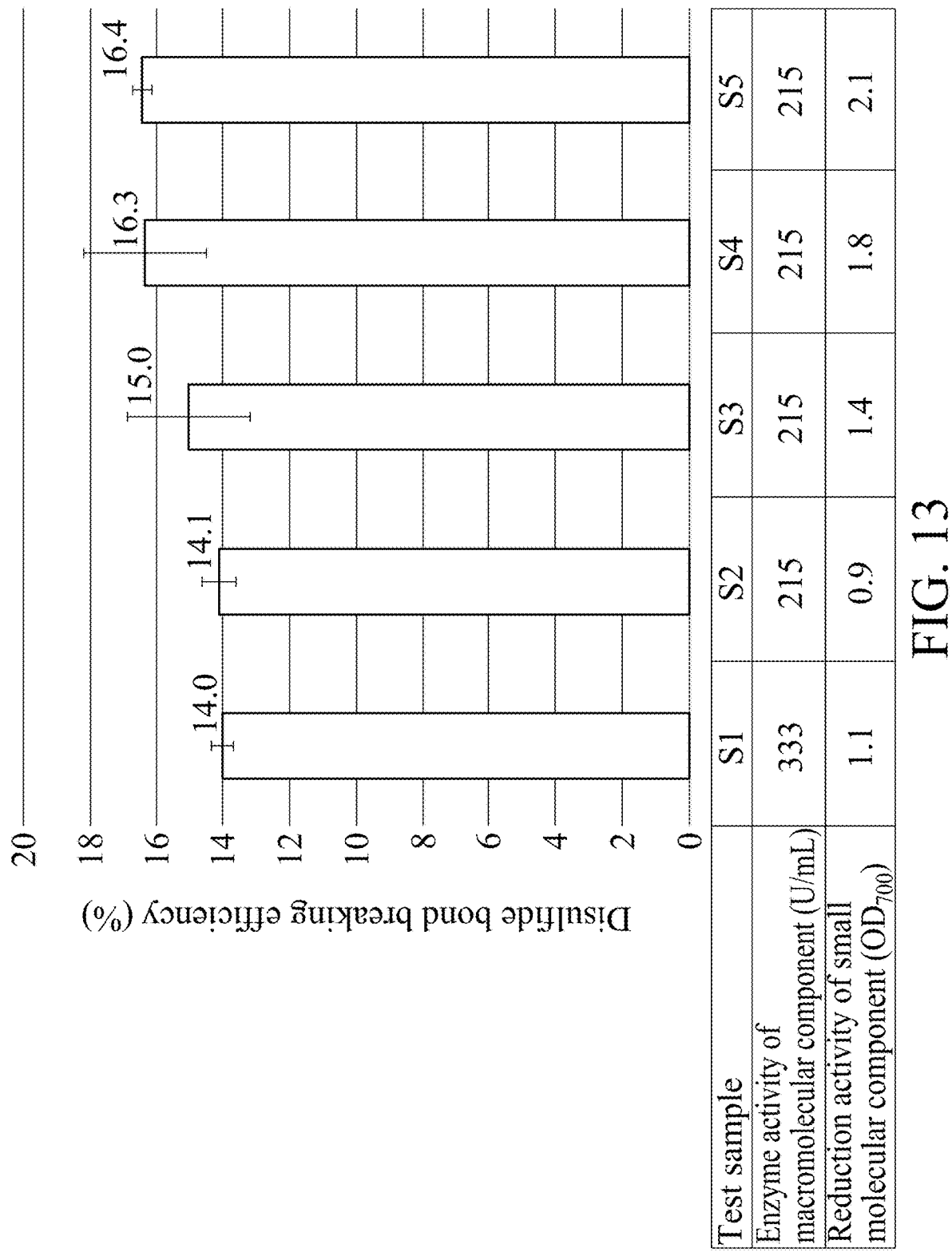
FIG. 13 shows the analysis of the disulfide bond breaking efficiency of different formulas of hair shape change compositions.

The results are show in FIG. 13.

According to FIG. 13, it is known that the foregoing 5 samples all have good disulfide bond breaking efficiency, wherein Sample S5 has the highest disulfide bond breaking efficiency, 16.4%.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A biological hair shape change composition, comprising:
   a macromolecular component, comprising:
   a protease belonging to the class of alkaline proteases;
   a small molecular component, comprising:
   a peptide with reduction activity; and
   an alkali agent component,
   wherein both the macromolecular component and the small molecular component are obtained from a fermentation product of *Bacillus licheniformis* and a keratin and/or keratin polymer-containing medium, and
   wherein molecular weights of ingredients in the macromolecular component are greater than or equal to 3 kDa and are 3-1000 kDa, and molecular weights of ingredients in the small molecular component are less than 3 kDa and are 0.01-2.99 kDa.

2. The biological hair shape change composition as claimed in claim 1, wherein the protease belonging to the class of alkaline proteases comprises alkaline protease, keratinase or a combination thereof.

3. The biological hair shape change composition as claimed in claim 1, wherein an activity of the protease belonging to the class of alkaline proteases is 150-3000 U/mL.

4. The biological hair shape change composition as claimed in claim 1, wherein the length of the peptide with reduction activity is 5-30 amino acids.

5. The biological hair shape change composition as claimed in claim 1, wherein the peptide with reduction activity comprises at least one of the following peptides:
   (a) a peptide comprising the amino acid sequence of SEQ ID NO. 1;
   (b) a peptide comprising the amino acid sequence of SEQ ID NO. 2;
   (c) a peptide comprising the amino acid sequence of SEQ ID NO. 3;
   (d) a peptide comprising the amino acid sequence of SEQ ID NO. 4;
   (e) a peptide comprising the amino acid sequence of SEQ ID NO. 5;
   (f) a peptide comprising the amino acid sequence of SEQ ID NO. 6;
   (g) a peptide comprising the amino acid sequence of SEQ ID NO. 7;
   (h) a peptide comprising the amino acid sequence of SEQ ID NO. 8;
   (i) a peptide comprising the amino acid sequence of SEQ ID NO. 9; and
   (j) a peptide comprising the amino acid sequence of SEQ ID NO. 10.

6. The biological hair shape change composition as claimed in claim 1, wherein the alkali agent component comprises a plant-derived alkali agent and/or a chemical synthesis-derived alkali agent.

7. The biological hair shape change composition as claimed in claim 6, wherein the plant-derived alkali agent comprises at least one of the following plant-derived alkali extracts:
   a water extract of coffee grounds, a water extract of tea stems, and a water extract of mulberry leaves.

8. The biological hair shape change composition as claimed in claim 1, wherein a concentration of the alkali agent component in the biological hair shape change composition is 1-80% (v/v).

9. The biological hair shape change composition as claimed in claim 1, wherein the *Bacillus licheniformis* comprises *Bacillus licheniformis* BCRC 14353, *Bacillus licheniformis* GI_5E-1 of which the deposit number is CCTCC M 20211045, or a combination thereof.

10. The biological hair shape change composition as claimed in claim 1, wherein the keratin and/or keratin polymer-containing medium comprise a keratin and/or keratin polymer-containing substance, and the keratin and/or keratin polymer-containing substance comprises feathers, hair, hooves, claws and/or horns of animals.

11. The biological hair shape change composition as claimed in claim 10, wherein the keratin and/or keratin polymer-containing substance comprises discarded feathers.

12. The biological hair shape change composition as claimed in claim 1, wherein a volume ratio of the macromolecular component to the small molecular component in the biological hair shape change composition is 5-10:1.5-3.

13. The biological hair shape change composition as claimed in claim 1, further comprising additional water.

14. A biological hair shape change kit, comprising:
   a macromolecular component, comprising:
   a protease belonging to the class of alkaline proteases;
   a small molecular component, comprising:
   a peptide with reduction activity;
   an alkali agent component; and
   at least one packaging container for containing the macromolecular component, the small molecular component and the alkali agent component,
   wherein both the macromolecular component and the small molecular component are obtained from a fermentation product of *Bacillus licheniformis* and a keratin and/or keratin polymer-containing medium,
   wherein molecular weights of ingredients in the macromolecular component are greater than or equal to 3 kDa and are 3-1000 kDa, and molecular weights of ingredients in the small molecular component are less than 3 kDa and are 0.01-2.99 kDa, and
   wherein the biological hair shape change kit is used in the form of a mixture of the macromolecular component, the small molecular component and the alkali agent component.

15. The biological hair shape change kit as claimed in claim 14, wherein the protease belonging to the class of alkaline proteases comprises alkaline protease, keratinase or a combination thereof.

16. The biological hair shape change kit as claimed in claim 14, wherein the length of the peptide with reduction activity is 5-30 amino acids.

17. The biological hair shape change kit as claimed in claim 14, wherein the peptide with reduction activity comprises at least one of the following peptides:
   (a) a peptide comprising the amino acid sequence of SEQ ID NO. 1;
   (b) a peptide comprising the amino acid sequence of SEQ ID NO. 2;
   (c) a peptide comprising the amino acid sequence of SEQ ID NO. 3;
   (d) a peptide comprising the amino acid sequence of SEQ ID NO. 4;
   (e) a peptide comprising the amino acid sequence of SEQ ID NO. 5;
   (f) a peptide comprising the amino acid sequence of SEQ ID NO. 6;
   (g) a peptide comprising the amino acid sequence of SEQ ID NO. 7;
   (h) a peptide comprising the amino acid sequence of SEQ ID NO. 8;

(i) a peptide comprising the amino acid sequence of SEQ ID NO. 9; and
(j) a peptide comprising the amino acid sequence of SEQ ID NO. 10.

18. The biological hair shape change kit as claimed in claim 14, wherein the alkali agent component comprises a plant-derived alkali agent and/or a chemical synthesis-derived alkali agent.

19. The biological hair shape change kit as claimed in claim 18, wherein the plant-derived alkali agent comprises at least one of the following plant-derived alkali agents:
a water extract of coffee grounds, a water extract of tea stems, and a water extract of mulberry leaves.

20. The biological hair shape change kit as claimed in claim 14, wherein the *Bacillus licheniformis* comprises *Bacillus licheniformis* BCRC 14353, *Bacillus licheniformis* GI_5E-1 of which the deposit number is CCTCC M 20211045, or a combination thereof.

21. The biological hair shape change kit as claimed in claim 14, wherein the keratin and/or keratin polymer-containing medium comprise a keratin and/or keratin polymer-containing substance, and the keratin and/or keratin polymer-containing substance comprises feathers, hair, hooves, claws and/or horns of animals.

22. The biological hair shape change kit as claimed in claim 21, wherein a content of the keratin and/or keratin polymer-containing substance in the keratin and/or keratin polymer-containing medium is 0.01-20 g/L.

23. The biological hair shape change kit as claimed in claim 21, wherein the keratin and/or keratin polymer-containing substance comprises discarded feathers.

24. The biological hair shape change kit as claimed in claim 14, wherein in the biological hair shape change kit, the macromolecular component is contained in a first agent, the small molecular component is contained in a second agent, and the alkali agent component is contained in a third agent, and
wherein the at least one packaging container comprises a first container, a second container and a third container, and the first agent is packaged in the first container, the second agent is packaged in the second container, and the third agent is packaged in the third container, and
wherein the biological hair shape change kit is used by mixing the first reagent, the second reagent and the third reagent.

25. The biological hair shape change kit as claimed in claim 24, wherein the biological hair shape change kit is used by mixing the first reagent, the second reagent, the third reagent and additional water in a volume ratio of 5-10:1.5-3:3-6:1-10.5.

26. The biological hair shape change kit as claimed in claim 24, wherein the biological hair shape change kit is used by respectively pouring the first reagent, the second reagent, and the third reagent all out of the first container, the second container, and the third container, and mixing them with additional water.

27. The biological hair shape change kit as claimed in claim 24, further comprising a mixing container for containing and mixing the first reagent, the second reagent, and the third reagent poured out of the first container, the second container, and the third container, respectively, and additional water.

28. The biological hair shape change kit as claimed in claim 14, wherein in the biological hair shape change kit, the macromolecular component and the small molecular component are contained in a first agent, and the alkali agent component is contained in a second agent, and
wherein the at least one packaging container comprises a first container and a second container, and the first agent is packaged in the first container and the second agent is packaged in the second container, and
wherein the biological hair shape change kit is used by mixing the first reagent and the second reagent.

29. The biological hair shape change kit as claimed in claim 28, wherein the biological hair shape change kit is used by mixing the first reagent, the second reagent, and additional water in a volume ratio of 6.5-13:3-6:1-10.5.

30. The biological hair shape change kit as claimed in claim 28, wherein the biological hair shape change kit is used by respectively pouring the first reagent, and the second reagent all out of the first container and the second container, and mixing them with additional water.

31. The biological hair shape change kit as claimed in claim 28, further comprising a mixing container for containing and mixing the first reagent and the second reagent poured out of the first container and the second container, respectively, and additional water.

32. The biological hair shape change kit as claimed in claim 14, wherein in the biological hair shape change kit, the macromolecular component, the small molecular component and the alkali agent component are contained in a first agent, and
wherein the at least one packaging container comprises a first container, and the first agent is packaged in the first container.

33. The biological hair shape change kit as claimed in claim 14, further comprising additional water.

34. A method for changing hair shape, comprising:
(a) a hair penetration step, wherein the biological hair shape change composition as claimed in claim 1 is applied to hair and allowed to penetrate into the hair; and
(b) a hair shape changing step, wherein hair has been applied with and penetrated by with the biological hair shape change composition or the mixture is subjected to a heating procedure to hydrolyze the backbone of a protein of the hair and break a disulfide bond in the protein of the hair to change the shape of the hair.

35. The method for changing hair shape as claimed in claim 34, wherein a temperature of the heating procedure is 40-100° C.

36. The method for changing hair shape as claimed in claim 34, wherein a temperature of the heating procedure is 60° C.

* * * * *

SEQUENCE LISTING

```
<160> NUMBER OF SEQ ID NOS: 10

<210> SEQ ID NO 1
<211> LENGTH: 14
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 1

Phe Thr Gln Ala Gly Ser Glu Val Ser Ala Leu Leu Gly Arg
1               5                   10
```

```
<210> SEQ ID NO 2
<211> LENGTH: 13
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 2

Val Asn Val Ala Asp Cys Gly Ala Glu Ala Leu Ala Arg
1               5                   10

<210> SEQ ID NO 3
<211> LENGTH: 22
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 3

Asp Val Ala Leu Ser Ser Gly Ser Ala Cys Thr Ser Ala Ser Leu Glu
1               5                   10                  15

Pro Ser Tyr Val Leu Arg
            20

<210> SEQ ID NO 4
<211> LENGTH: 13
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 4

Trp Glu Leu Leu Gln Gln Gln Gly Pro Ser Gly Pro Arg
1               5                   10

<210> SEQ ID NO 5
<211> LENGTH: 11
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 5

Gln Ser Val Glu Ala Asp Ile Asn Gly Leu Arg
1               5                   10

<210> SEQ ID NO 6
<211> LENGTH: 15
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 6

Val Gly Tyr Ala Val Cys Gln Ile Asn Leu Gly Leu Ser Gln Arg
1               5                   10                  15

<210> SEQ ID NO 7
```

```
<211> LENGTH: 12
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 7

Ser Leu Asp Leu Asp Ser Ile Ile Ala Glu Val Lys
1               5                   10

<210> SEQ ID NO 8
<211> LENGTH: 25
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 8

Leu Ile Ser Gly Glu His Val Gly Ala Leu Ala Met Ser Glu Pro Asn
1               5                   10                  15

Ala Gly Ser Asp Val Val Ser Met Lys
            20                  25

<210> SEQ ID NO 9
<211> LENGTH: 12
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 9

Val Gly Ala Leu Thr Asp Glu Ile Asn Phe Leu Arg
1               5                   10

<210> SEQ ID NO 10
<211> LENGTH: 23
<212> TYPE: PRT
<213> ORGANISM: Unknown
<220> FEATURE:
<223> OTHER INFORMATION: A small molecule peptide with reduction
      activity from a fermentation product of Bacillus licheniformis and
      a medium containing feathers

<400> SEQUENCE: 10

Leu Cys Tyr Val Ala Leu Asp Phe Glu Gln Glu Met Ala Thr Ala Ala
1               5                   10                  15

Ser Ser Ser Ser Leu Glu Lys
            20
```